United States Patent [19]

Gilon et al.

[11] Patent Number: 5,723,575
[45] Date of Patent: Mar. 3, 1998

[54] PROCESS FOR THE PREPARATION OF BACKBONE CYCLIC PEPTIDES

[75] Inventors: Chaim Gilon; Zvi Zelinger; Gerardo Byk, all of Jerusalem, Israel

[73] Assignee: Yissum Research Development Company of the Hebrew University of Jerusalem, Jerusalem, Israel

[21] Appl. No.: 444,135

[22] Filed: May 18, 1995

Related U.S. Application Data

[63] Continuation of Ser. No. 955,380, Oct. 1, 1992, abandoned.

[30] Foreign Application Priority Data

Oct. 2, 1991 [IL] Israel ............................ 99628

[51] Int. Cl.[6] .................. C07K 1/00; C07K 1/02; C07K 1/04; C07K 5/12
[52] U.S. Cl. ............ 530/317; 525/54.11; 530/333; 530/334; 530/338
[58] Field of Search .................. 530/317, 324, 530/337, 345, 333, 334, 338; 525/54.11

[56] References Cited

U.S. PATENT DOCUMENTS 4,985,406   1/1991   Charpentier et al. ............ 530/317
5,169,935  12/1992   Hoeger et al. .................. 530/334

FOREIGN PATENT DOCUMENTS 0444898   9/1991   European Pat. Off. ............ 530/317
0150199   8/1981   Germany ...................... 530/317
2216529  10/1989   United Kingdom ................ 530/317

OTHER PUBLICATIONS

Gilon et al. "Backbone cyclization: A new method for conferring conformational constraint on peptides." Biopolymers 31: 745–750, 1991.
Anwer, et al., *Communications* 929–932, Nov. 1980.
Atherton, et al., *Bioorganic Chemistry* 8:351–370, 1979.
Bergmann, et al., *Über ein allgemeines Verfahren der Peptid–Synthese* 65:1192–1201, 1932.
Charpentier, et al., *J. Med. Chem.* 32:1184–1190, 1989.
Darman, et al., *Biochemical and Biophysical Research Communications*, No. 2, 127:656–662, 1985.
Gilon, et al., *Biopolymers* 31:745–750, 1991.
Hruby, *Life Sciences* 31:189–199, 1982.
Kaiser, et al., *Short Communications*, 595–598.
Kessler, et al., *Angew. Chem. Int. Ed. Engl.*, No. 11, 25:997–1002, 1986.
Kessler, *Angew. Chem. Int. Ed. Engl.* 21:512–523, 1982.
Krieger, *Science* 222:975–985, 1983.
Laufer, *The Journal of Biological Chemistry*, No. 22, 261:10257–10263, 1986.

Levian–Teitelbaum, et al., *Biopolymers* 28:51–64, 1989.
Ludescher, et al., *Helvetica Chimica Acta*, vol. 54, Fasc. 6 (1971), Nr. 173–174, pp. 1637–1644.
Manesis, et al., *J. Org. Chem.* 52:5331–5341, 1987.
Milner–White, *TiPS* 10:70–74, 1989.
Nagasawa, et al., *Bulletin of the Chemical Society of Japan* 46:1269–1272, 1973.
Al–Obeidi, et al., *J. Med. Chem.* 32:2555–2561, 1989.
Snyder, *Science* 209:976–983, 1980.
Theodoropoulos, et al., *J. Med. Chem.* 28:1536–1539, 1985.
Van der Auwera, et al., *Int. J. Peptide Protein Res.* 29:574–588, 1987.
Veber, et al., *TINS*, 392–396, 1985.
Kaiser, et al., *Anal. Biochem.* 34: 595–598, 1970.

*Primary Examiner*—Douglas W. Robinson
*Assistant Examiner*—Amy T. Nelson

[57] ABSTRACT

Biologically active, backbone-cyclized peptides of the formula:

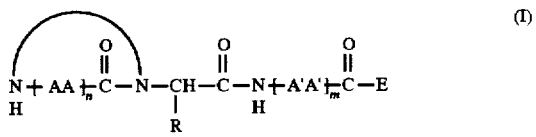

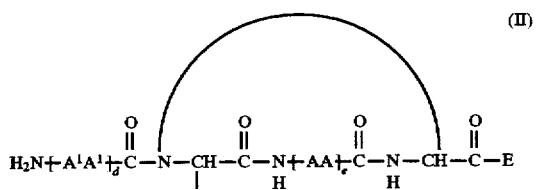

wherein [AA] or $[A^1A^1]$ is a naturally occurring or synthetic amino acid residue, n or e is an integer of 1–10, m or d is 0 or an integer of 1–10, R is a naturally occurring or synthetic amino acid side-chain, E is a hydroxyl moiety or a carboxyl protecting group of a blocking group, optionally covalently attached to an insoluble polymeric support, and the circled line designates a spacer group of

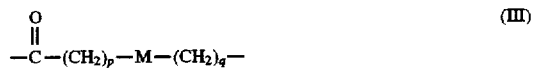

for formula I wherein M is —S—S—, —CO—NH— or —S— and p and q each is an integer of 2–10, or

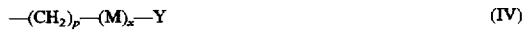

for formula II wherein M is an amino or carboxyl group or a sulfur atom, p is an integer of 2–10, x is 0 or 1 and Y is a side-chain of a backbone amino acid. Also, processes for the preparation of these peptides and pharmaceutical compositions containing them.

21 Claims, 3 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
  (A) LENGTH: 5 amino acids
  (B) TYPE: amino acid
  (C) STRANDEDNESS: single
  (D) TOPOLOGY: linear (ii) MOLECULE TYPE: peptide (ix) FEATURE:
  (A) NAME/KEY: Modified-site
  (B) LOCATION: 2
  (D) OTHER INFORMATION: /label=Xaa
  / note= "Xaa = Phe or Val"

(xi) SEQUENCE DESCRIPTION: SEQ ID NO:1:

Phe Xaa Gly Leu Met
1               5

(2) INFORMATION FOR SEQ ID NO:2:

(i) SEQUENCE CHARACTERISTICS:
  (A) LENGTH: 11 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:2:

Arg Pro Lys Pro Gln Gln Phe Phe Gly Leu Met
1               5                   10

PROCESS FOR THE PREPARATION OF BACKBONE CYCLIC PEPTIDES

This is a continuation of application Ser. No. 07/955,380, filed Oct. 1, 1992, now abandoned.

FIELD OF THE INVENTION

The present invention relates to biologically active, backbone-cyclized peptides, to processes for their preparation and to pharmaceutical compositions containing them.

More particularly, the peptides of the invention are of general formulae (I) and (II):

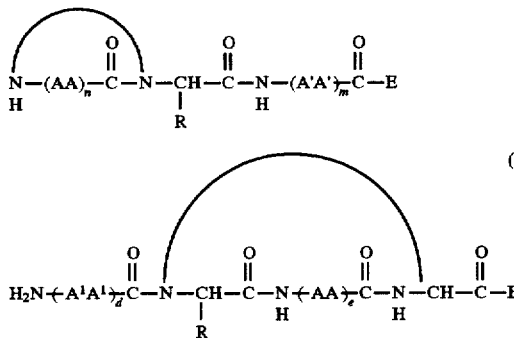

wherein the substituents and circled line are as hereafter defined.

BACKGROUND OF THE INVENTION

Following the pioneering work of R. Schwyzer Ludecher, U., et al., Helv. Chim. Acta 54, 1637 (1971)) on gramicidin S, conformational restriction of peptides by medium and long range cyclization has been extensively employed. In addition to other modes of conformational restriction, such as configurational and structural alteration of amino acids, local backbone modifications, short-range cyclization etc., medium and long range cyclization (Hruby, V. J., Life Sci. 31, 189 (1982); Kessler, H., Angew. Chem. Int. Ed. Eng., 21, 512 (1982); Schiller, P. W., in the "Peptides", Udenfriend, S., and Meienhofer, J. Eds., Volume 6 p. 254 (1984); Veber, D. F. and Freidinger, R. M., Trends in Neurosci. 8, 392 (1985); Milner-White, E. J., Trends in Pharm. Sci. 10, 70 (1989)) is used for the following purposes: biologically active peptides are cyclized to achieve metabolic stability, to increase potency, to confer or improve receptor selectivity and to control bioavailability. The possibility of controlling these important pharmacological characteristics through cyclization of linear peptides prompted the use of medium and long range cyclization to convert natural bioactive peptides into peptidomimetic drugs. Cyclization also brings about structural constraints that enhance conformational homogeneity and facilitate conformational analysis (Kessler, H., Angew. Chem. Int. Ed. Eng., 21, 512 (1982)). Moreover, the combination of structural rigidification-activity relationship studies and conformational analysis gives insight into the biologically active conformation of linear peptides.

In addition to other restrictive methods such as template associated synthetic proteins (Mutter, M., and Vuilleumier, S., Angew. Chem. Int. Ed. Eng., 101, 551(1982)), medium and long range cyclizations are also used for controlled stabilization of secondary and tertiary structures of proteins.

Small, linear, biologically active peptides usually exist in solution in a fast equilibrium of interchanging conformations (Kessler, H., Angew. Chem. Int. Ed. Eng., 21, 512 (1982)), which may lead to lack of receptor selectivity and metabolic susceptibility (Veber, D. F. and Freidinger, R. M., Trends in Neurosci. 8, 392 (1985)). Moreover, this fast equilibrium also hampers attempts to determine their conformations in solution including the biologically active conformation. For example, a given linear peptide can exist in solution in a fast equilibrium of conformer A, which activates receptor A, conformer B, which activates receptor B and in an extended conformation C which fits into the active-site of a degrading enzyme. Structural modifications that slow down the fast equilibrium and reduce the conformational space impose conformational constraints on linear peptides (Kessler, H., Angew. Chem. Int. Ed. Eng., 21, 512 (1982)).

Ideally the best modification, from a biological standpoint, slows down the equilibrium or reduces the conformational space to such an extent that the peptide will interact only with receptor A and will not attain either the conformation that activates receptor B or the extended degradable conformation C. If an attempt is made to determine the active conformation, further restrictions might be needed. Experimental evidence for the validity of the theorem presented above can be found in the cases of the enkephalins, somatostatin, gonadotropin releasing hormone (GnRH), cholecystokinin (CCK), melanocyte stimulating hormone (αMSH) and many other peptides in which cyclization results in receptor selectivity and metabolic stability (Hruby, V. J., Life Sci. 31, 189 (1982); Kessler, H., Angew. Chem. Int. Ed. Eng.,21, 512 (1982); Schiller, P. W., in the "Peptides", Udenfriend, S., and Meienhofer, J. Eds., Volume 6 p. 254 (1984); Veber, D. F. and Freidinger, R. M., Trends in Neurosci. 8, 392 (1985); Milner-White, E. J., Trends in Pharm. Sci. 10, 70 (1989); Al-Obbeidi, F., et al., J. Med. Chem., 32, 2555 (1989); Charpentier, B., et al., J. Med. Chem., 32 1184 (1989); Rivier, J. E., et al., in "peptides", Rivier, J. E., and Marshall, G. R. Eds., p. 33 (1990)) and in very few cases even allowed conformational analysis of the bioactive conformation (Kessler, H., Angew. Chem., 25 997 (1986)).

Conformationally restricted peptides containing medium and long range cyclizations have been mainly prepared following the same modes of cyclization of homodetic and heterodetic natural peptides. These include: a side-chain to side-chain cyclization (usually the formation of a lactam ring and/or an —S—S— bond through cyclization of functional groups already present in the native sequence or by substitution of other amino acids with Glu and Lys or Cys respectively); b end to end cyclization (previously called backbone to backbone cyclization (Manesis, N. J. and Goodman, M., Org. Chem., 52, 5331 (1987))) and c sidechain to end groups cyclization.

The last mode of cyclization includes side-chain to amino end and side-chain to carboxyl end. The exact location, type and size of the ring (which can also be controlled by "spacers" (Manesis, N. J. and Goodman, M., Org. Chem., 52, 5331 (1987))) to achieve maximum selectivity and activity is determined mainly by Structure-Activity-Relationship (SAR) considerations in conjunction with conformational analysis.

Despite the impressive success achieved hitherto with cyclic peptides, cyclization according to the above modes, caused in some the loss of biological activity especially if carried out in the "active region" of bioactive peptides. A typical example is the case of substance P (SP) and its related peptides the mammalian tachykinins neurokinin A (NKA) and neurokinin B (NKB). The tachykinins are short linear peptides (ten to eleven amino acid residues) which share the common carboxyl terminal sequence -Phe-X-Gly-Leu-Met-NH$_2$ (X=Phe or Val) (SEQ ID NO:1). The amino acid sequence of Substance P is the following:

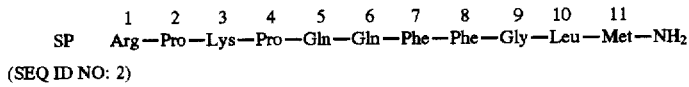

SP  Arg—Pro—Lys—Pro—Gln—Gln—Phe—Phe—Gly—Leu—Met—NH$_2$
     1    2    3    4    5    6    7    8    9   10   11

(SEQ ID NO: 2)

(the positions of the amino acid residues in SP will be used in the description and Examples hereafter).

SP and the other tachykinins have been implicated in a variety of physiological functions, including transmission of pain stimuli, glandular secretion, intestinal motility, vasodilation, inflammatory pain reaction and a large variety of behavioral effects. The tachykinins activate three receptors NK-1, NK-2 and NK-3 (Trends Pharm. Sci. Receptor Nomenclature Supplement p. 25 (1990)). The mammalian tachykinins are not selective in the sense that each one of them activates more than one receptor. Thus, for example NKB activates the NK-1 and the NK-3 receptors with comparable potency (EC$_{50}$(nM) of 4.2 and 1.3 respectively (Papir-Kricheli, D., et al., Pain, 31, 263 (1987))).

In addition to their lack of selectivity the mammalian tachykinins are degraded rapidly especially in in vivo assays (Wormser, U., et al., in "peptides 1984" Ragnarsson, U., Ed. p. 359 (1985)).

The present inventors have prepared two conformationally constrained linear hexapeptide analogs of the carboxyl terminal sequence of SP, which incorporate N-alkylated amino acids, which showed receptor selectivity. The NK-3 selective analog Senktide (Laufer, R., et al., J. Biol. Chem., 22, 10257 (1986)) (succ(Asp$^6$, N-Me Phe$^8$)SP$_{6-11}$, EC$_{50}$ (nM) NK-3: 0.5, NK-2: >200,000, NK-1: 35,000) and the NK-1 selective analog WS Septide (Papir-Kricheli, D., et al., Pain, 31, 263 (1987)) (Ac(Arg$^6$, Pro$^9$)SP$_{6-11}$, EC$_{50}$(nM) NK-1: 3.0, NK-2: >200,000, NK-3: >100,000). Senktide is metabolically stable in all tissues tested whereas WS Septide is metabolically unstable (half life of few minutes in liver, kidneys and parotid slices).

The present inventors have attempted to use the two selective analogs Senktide and WS Septide to elucidate the conformational requirements of the NK-3 and NK-1 receptors respectively. For this purpose they built tentative molecular models of Senktide and WS Septide based on NMR studies (Levian-Teitelbaum, D., et al., Biopolymers, 28, 51 (1989)). To correlate the molecular models of Senktide and WS Septide to the bioactive conformation, additional conformational constraints, such as cyclization could be imposed. Provided these more rigid analogs maintain their bioactivity and selectivity, they could be subjected to further conformational analysis. Attempts to cyclize the active region of SP, namely the C-terminal hexapeptide, resulted in biologically inactive compounds (Neubert, K., et al., Pharmazie 40, 617 (1985); Chassing, G., et al., in "peptides 1984" Ragnarsson, U., Ed. p. 345 (1985); Sandberg, B. E. B., et al., in "peptides 1984" Ragnarsson, U., Ed. p. 369 (1985); Theodoropoulos, D., et al., J. Med. Chem., 28, 1536 (1985); Drmen, P. S., et al., Biochem. Biophys. Res. Commun., 127, 656 (1985); Mutulis, F., et al., Bioorg. Chim., 11, 1276 (1985)).

In a theoretical article (Gilon, C., et al., Biopolymers, 31, 745 (1991)) the inventors present a new general concept of cyclization, employing WS Septide as model peptide. The proposed new cyclization method has been termed "backbone cyclization" and is discussed in detail in said article. Few of the cyclized peptides subject of the present invention are generally disclosed in said article, however the article does not propose any method for the preparation of the present compounds.

Subsequent work by the present group of inventors led to the preparation of the present novel cyclized peptides. Notwithstanding the fact that the objects to be achieved by cyclization were well defined, and although the theoretical SAR consideration were taken into account, great efforts were involved in aiming at the novel, biologically active and selective peptides. The SP analogs which will be specifically exemplified hereafter are to be considered as models for the universal cyclization methods disclosed, and the cyclic peptides prepared thereby.

Neuropeptides control a wide range of endocrinological, motoric and behavioral activities (Krieger, D. T., Science 222, 975–978 (1983); Snyder, S. H. Science 209, 976 (1980)). These substances mediate a large variety of physiological functions including analgesia, appetite control, thirst, body temperature, mood, learning, neurological behavior, pain and modulation of immune response. Thus derivatives of the naturally occurring neuropeptides, both as agonists or antagonists, have a great potential in the prevention and treatment of many neurological and behavioral disorders.

However, despite many attempts, there are only few ligands which are used therapeutically. The prior attempts were mainly directed at imitating the biological activity of the naturally occurring peptides. In order to design and synthesize a therapeutical agent which would control and/or modulate said activity, many factors are to be taken into account. Information regarding the bioactive conformation of the peptide is important. The peptides can occur in different conformations, each of which is specific for a different receptor. In addition to the desired biological activity, lack of conformational stability would result in association with undesired receptors, and with undesired side-effects. The bioactive conformation of only very few of the many known neuropeptides has yet been established.

Neuropeptides undergo fast proteolytic degradation in the gastrointestinal tract, in blood and in other tissues. The pharmacokinetics of neuropeptides in the synapse are completely different from those of a therapeutic peptide. In the synapse, the time required for the neuropeptides to accomplish their function is very short due to the short distance involved. The endogenous proteases which are responsible for terminating the activity of a certain neuropeptide are the only ones present in the vicinity, and they degrade the peptide immediately after completion of its function. In order to devise a "therapeutical peptide", its structure should be stabilized against the proteases responsible for its degradation, as well as against other proteases present in the GI tract, blood and other tissues.

Natural peptides do not easily cross the GI/blood and blood/brain barriers. This problem cannot be secluded from that of metabolic stability. Crossing both the GI/blood and blood/brain barriers are key steps when considering using a peptide as a drug. While several peptides were successfully stabilized against degradation, their bioavailability, namely crossing the blood/brain barrier remained a mystery. In addition, different receptors induce different physiological activities, therefore triggering an undesired receptor by the peptide would cause undesired side-effects. The common hypothesis is that a linear peptide is in a state of fast equilibrium between a large number of conformations, some of which would activate undesired receptors. Also, the peptide has to be in the right conformation in order to undergo enzymatic degradation. Only the desired conformation, termed the bioactive conformation, would activate the desired receptor and result in only the specific biological activity which is wanted.

These problems of naturally occurring peptides, such as, for example, neuropeptides are of great significance and constitute major problems in applying the peptide as a drug, as well as understanding the pharmacological and molecular interaction between the peptide and its receptor.

Successful prior art results, for example the analgesic peptidomimetic opiates, which are "imitations" of endogenous enkephalins, were achieved through works which were more random than rationally planned and did not take into consideration all the factors described above.

SUMMARY OF THE INVENTION

The invention relates to backbone cyclized, biologically active polypeptides of the general formula:

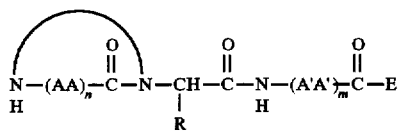

(I)

wherein n designates an integer of from 1 to 10;

m designates 0 or an integer of from 1 to 10;

(AA) designates a naturally occurring or synthetic amino acid residue, wherein when n is greater than 1, the amino acid residues may be the same or different;

($A^1A^1$) designates a naturally occurring or synthetic amino acid residue, wherein when m is greater than 1, the amino acid residues may be the same or different;

R designates a naturally occurring or synthetic amino acid side-chain;

E represents a hydroxyl, or a carboxyl protecting group which is standard in peptide synthesis (e.g. Schroeder et al., "The Peptides", Vol. I, Academic Press, 1965; or Bodanszky, "Principles of Peptide Synthesis", Springer-Verlag, 1984; or Bodanszky et al., "the Practice of Peptide Synthesis", Springer-Verlag, 1984; or McOmie (ed.), "Protective Groups in Organic Chemistry", Plenum Press, 1973; or Greene, "Protective Groups in Organic Synthesis", Wiley-Interscience, 1981; or Barany and Merrifield, in "The Peptides: Analysis, Synthesis and Biology", Vol. 2, Chapter 1, Academic Press, 1980), preferably selected from alkoxy, substituted alkoxy or aryloxy, or a blocking group which may be the same as the carboxyl group or an amino or substituted amino group, wherein the carboxyl protecting or blocking group may be optionally covalently attached to an insoluble polymeric support, and the circled line designates a spacer group of the formula:

$$-C-(CH_2)_p-M-(CH_2)_q-$$ (III)

with O above the C, wherein M is selected from the group consisting of —S—S—, —CO—NH— and —S— and p and q, which may be the same or different, each designates an integer of from 2 to 10; or to backbone cyclized, biologically active polypeptides of the general formula:

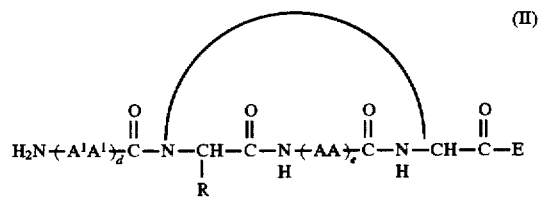

(II)

wherein d is 0 or an integer of from 1 to 10 and e is an integer of from 1 to 10;

(AA) designates a naturally occurring or synthetic amino acid residue, wherein when e is greater than 1, the amino acid residues may be the same or different;

($A^1A^1$) designates a naturally occurring or synthetic amino acid residue, wherein when d is greater than 1, the amino acid residues may be the same or different;

R designates a naturally occurring or synthetic amino acid side-chain;

E represents a hydroxyl, or a carboxyl protecting group which is standard in peptide synthesis, preferably selected from alkoxy, substituted alkoxy or aryloxy, or a blocking group which may be the same as the carboxyl group or an amino or substituted amino group, wherein the carboxyl protecting or blocking group may be optionally covalently attached to an insoluble polymeric support, and the circled line designates a spacer group of the formula:

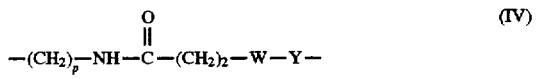

(IV)

wherein p is as defined above, Z is an integer from 0 to 10, Y designates the side-chain of Asp, Glu, Cys or Met, and W is sulfur or an amino, amide carboxyl or disulfide group.

In the compounds of formula I, M as defined in formula III is preferably an amide or —S—S— group.

In the compounds of formula II, Y as defined in formula IV is preferably the side chain of homocysteine, p is preferably 3 or 4, q is preferably 3 and W is preferably a sulfur atom.

In the compounds of both general formulae I and II, E is preferably an amino group.

BRIEF DESCRIPTION OF DRAWING FIGURES

DETAILED DESCRIPTION OF THE INVENTION

Throughout this application the various groups

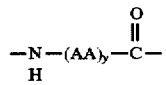

designate an amino-acid residue, the NH constitute the N-terminus and the CO the C-terminus in the peptidic chain, where y is 1 or greater than 1. It is to be understood, that where y is defined as zero, the whole group HN—(AA)—CO is absent.

Preferred specific cyclized peptides, which serve herein as a model for the present cyclopeptides and the processes for their preparation are homologs of neuropeptides, more specifically of Substance P. Preferred peptides according to formula I are:

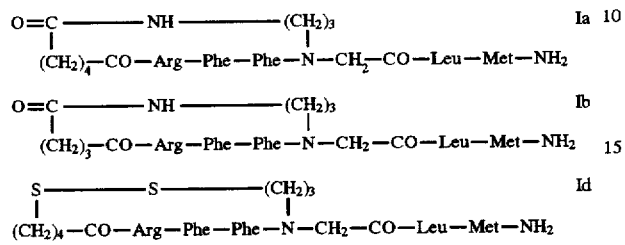

A preferred peptide according to formula II is:

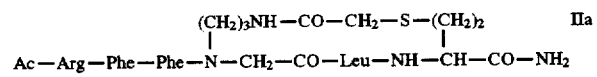

Figure 1:
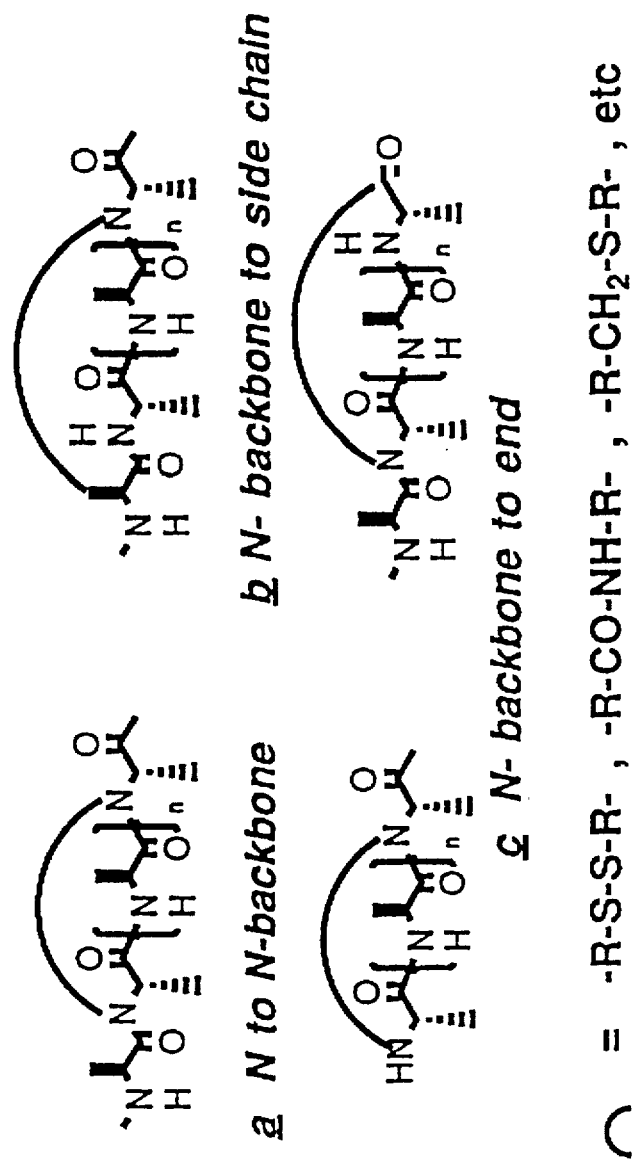
FIG. 1 Illustrates the concept of backbone cyclization.

Backbone cyclization according to the present invention involves the joining of the $N^\alpha$ and/or the $C^\alpha$ atoms in the peptidic backbone. The concept of N-backbone cyclization is shown in FIG. 1. Thus, for example, to achieve N-backbone cyclization, hydrogens of the peptide bond are replaced by ω-functionalized alkylene chains that can then be either connected to side-chains or ends or interconnected to form the desired cyclic peptide.

The invention thus also relates to processes for the preparation of cyclic peptides of the general formulae I and/or II, according to the following schemes.

The preparation of compounds of general formula I comprises the steps of:
Scheme 1

(a) reacting a compound of the formula:

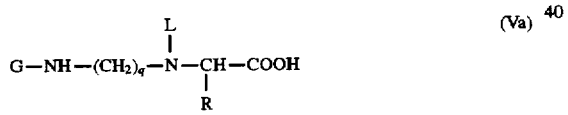

wherein q
represents an integer of from 2 to 10, G and L, which may be the same or different, each represents a protecting group conventional in peptide synthesis (e.g. Schroeder et al., "The Peptides", Vol. I, Academic Press, 1965; or Bodanszky, "Principles of Peptide Synthesis", Springer-Verlag, 1984; or Bodanszky et al., "the Practice of Peptide Synthesis", Springer-Verlag, 1984; or McOmie (ed.), "Protective Groups in Organic Chemistry", Plenum Press, 1973; or Greene, "Protective Groups in Organic Synthesis", Wiley-Interscience, 1981; or Barany and Merrifield, in "The Peptides: Analysis, Synthesis and Biology", Vol 2 Chapter 1, Academic Press, 1980), with an amino acid or a polypeptide of the formula $H_2N-(A^1A^1)_m-CO-E$, wherein m integer from 1 to 10 and $A^1A^1$ represents a naturally occurring or synthetic amino acid residue, the amino acid residues where m is greater than 1 being the same or different, and E represents a hydroxyl, or a carboxyl protecting group which is standard in peptide synthesis, preferably selected from alkoxy, substituted alkoxy or aryloxy, or a blocking group which may be the same as the carboxyl group or an amino or substituted amino group, wherein the carboxyl protecting or blocking group may be optionally covalently attached to an insoluble polymeric support, to give a compound of the formula:

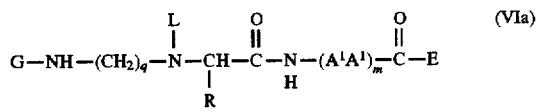

b) selectively removing from the compound of formula VIa, protecting group L, to give a compound of the formula:

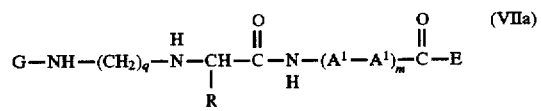

c) reacting the compound of formula VIIa with an amino acid or peptide of the formula:

wherein n is an integer of from 1 to 10, (AA) represents a naturally occurring or synthetic amino acid residue, the amino acid residues where n is greater than 1 being the same or different and J represents a protecting group conventional in peptide synthesis to give a compound of the formula:

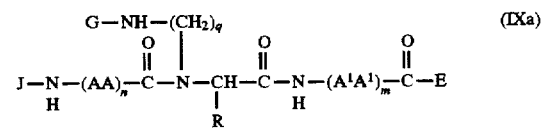

d) selectively removing the protecting group J to give a compound of the formula:

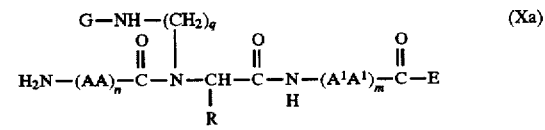

e) reacting the compound of formula X with a compound of the formula:

wherein p is as defined above to give a compound of the formula:

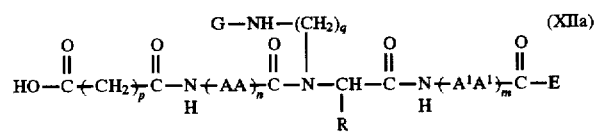

f) selectively removing from the compound XII the protecting group G to give a compound of the formula:

$$\text{(XIIa)} \quad HO-\overset{O}{\overset{\|}{C}}(CH_2)_{p}\overset{O}{\overset{\|}{C}}-\underset{H}{N}-(AA)_{n}\overset{O}{\overset{\|}{C}}-\underset{H}{\overset{H_2N-(CH_2)_q}{N}}-CH-\overset{O}{\overset{\|}{C}}-\underset{H}{N}(A^1A^1)_{m}\overset{O}{\overset{\|}{C}}-E$$
$$\underset{R}{}$$

g) reacting the compound of formula XIIIa with a suitable coupling agent according to standard methods of peptide synthesis and removing other side-chain protecting groups to give a compound of the general formula I where m is an integer from 1 to 10.

Scheme 2

(a) selectively removing the protecting group L from the compound of formula:

$$\text{(Vb)} \quad G-NH-(CH_2)_q-\underset{R}{\overset{L}{\underset{|}{N}}}-CH-\overset{O}{\overset{\|}{C}}-E$$

wherein q represents an integer of from 2 to 10, G and L, which may be the same or different, each represents hydrogen and/or a protecting group conventional in peptide synthesis, and E represents a hydroxyl, or a carboxyl protecting group which is standard in peptide synthesis, preferably selected from alkoxy, substituted alkoxy or aryloxy, or a blocking group which may be the same as the carboxyl group or an amino or substituted amino group, wherein the carboxyl protecting or blocking group may be optionally covalently attached to an insoluble polymeric support to give a compound of the formula:

$$\text{(VIb)} \quad G-NH-(CH_2)_q-\overset{H}{\underset{|}{N}}-\underset{R}{CH}-\overset{O}{\overset{\|}{C}}-E$$

b) reacting the compound of formula VIb with an amino acid or peptide of the formula:

$$\text{(VIIb)} \quad J-\underset{H}{N}-(AA)_n-\overset{O}{\overset{\|}{C}}-OH$$

wherein n is an integer from 1 to 10, (AA) represents a naturally occurring or synthetic amino acid residue, the amino acid residues where n is greater than 1 being the same or different and J represents a protecting group conventional in peptide synthesis, to give a compound of the formula:

$$\text{(VIIIb)} \quad J-\underset{H}{N}-(AA)_n\overset{O}{\overset{\|}{C}}-\underset{|}{\overset{G-NH-(CH_2)_q}{N}}-CH-\overset{O}{\overset{\|}{C}}-E$$
$$\underset{R}{}$$

c) selectively removing the protecting group J to give a compound of the formula:

$$\text{(IXb)} \quad H_2N-(AA)_n\overset{O}{\overset{\|}{C}}-\underset{|}{\overset{G-NH-(CH_2)_q}{N}}-CH-\overset{O}{\overset{\|}{C}}-E$$
$$\underset{R}{}$$

d) reacting the compound of formula IXb with a compound of the formula XI to give a compound of the formula:

$$\text{(Xb)} \quad HO-\overset{O}{\overset{\|}{C}}-(CH_2)_p-\overset{O}{\overset{\|}{C}}-\underset{H}{N}-(AA)_n\overset{O}{\overset{\|}{C}}-\underset{|}{\overset{G-NH-(CH_2)_q}{N}}-CH-\overset{O}{\overset{\|}{C}}-E$$
$$\underset{R}{}$$

e) selectively removing from the compound Xb the protecting group G to give a compound of formula:

$$\text{(Xb)} \quad HO-\overset{O}{\overset{\|}{C}}-(CH_2)_p-\overset{O}{\overset{\|}{C}}-\underset{H}{N}-(AA)_n\overset{O}{\overset{\|}{C}}-\underset{|}{\overset{G-NH-(CH_2)_q}{N}}-CH-\overset{O}{\overset{\|}{C}}-E$$
$$\underset{R}{}$$

f) reacting the compound of formula XIb with a coupling agent as described for (g) above to give a compound of general formula I wherein m equals 0.

The preparation of compounds of the general formula II comprises the steps of:

a) reacting a compound of the formula:

$$\text{(XIV)} \quad H_2N-(A'A')_e-\overset{O}{\overset{\|}{C}}-\underset{H}{\overset{Q-Y}{\underset{|}{N}}}-CH-\overset{O}{\overset{\|}{C}}-E$$

wherein E and e are as defined above, $(A^1A^1)$ represent a naturally occurring or synthetic amino acid residue and Y represents a side-chain of naturally occurring or synthetic amino acid and Q represents a protecting group conventional for peptide synthesis with a compound of formula Va, to give a compound of the formula:

$$\text{(XV)} \quad G-NH-(CH_2)_q-\overset{L}{\underset{|}{N}}-\underset{R}{CH}-\overset{O}{\overset{\|}{C}}-\underset{H}{N}-(A'A')_e-\overset{O}{\overset{\|}{C}}-\underset{H}{\overset{Q-Y}{\underset{|}{N}}}-CH-\overset{O}{\overset{\|}{C}}-E$$

b) selectively removing from the compound of formula XV protecting group L, to give a compound of the formula:

$$\text{(XVI)} \quad G-NH-(CH_2)_q-\overset{H}{\underset{|}{N}}-\underset{R}{CH}-\overset{O}{\overset{\|}{C}}-\underset{H}{N}-(A'A')_e-\overset{O}{\overset{\|}{C}}-\underset{H}{\overset{Q-Y}{\underset{|}{N}}}-CH-\overset{O}{\overset{\|}{C}}-E$$

c) reacting the compound of formula XVI with an amino acid or peptide of the formula:

$$\text{(XVII)} \quad P-NH-(AA)_d-COOH$$

wherein d is an integer from 1 to 10 and (AA) represents a naturally occurring or synthetic amino acid residue, the amino acid residues where d is greater than 1 being the same or different, and P represents a protecting group conventional in peptide synthesis, to give a compound of the formula:

$$\text{(XVIII)} \quad P-NH-(AA)_d-CO-\underset{|}{\overset{(CH_2)_q-NH-G}{N}}-CH-\overset{O}{\overset{\|}{C}}-\underset{H}{N}-(A'A')_e-\overset{O}{\overset{\|}{C}}-\underset{H}{\overset{Q-Y}{\underset{|}{N}}}-CH-\overset{O}{\overset{\|}{C}}-E$$
$$\underset{R}{}$$

d) (i) where Y is a carboxyl bearing side-chain, selectively removing the protecting groups G and Q from compound XVIII to give a compound of the formula:

$$\underset{R}{\overset{(CH_2)_q-NH_2}{P-NH(-AA)_d CO-N-CH-C-N(-A'A')_r C-N-CH-C-E}} \quad (XIX)$$

cyclizing the compound XIX as described in step g) above and removing protecting group P and other side-chain protecting groups to give a compound of the general formula II; or (ii) where Y is a side-chain bearing a nucleophilic functional group, selectively removing protecting group G, reacting the resulting compound with a compound of the formula:

$$HOOC-(CH_2)_z-W \quad (XX)$$

wherein z is an integer from 1 to 10 and W is a functional group capable of reacting with said nucleophilic group Y, preferably selected from the group consisting of halogen atoms, O-p-toluene sulphonyl, O-methanesulphonyl an O-trifluoromethane sulphonyl, to give a compound of the formula:

$$(XXI)$$
$$\underset{R}{\overset{(CH_2)_q-N-CO-(CH_2)_2-W}{P-NH(-AA)_d CO-N-CH-C-N(-A'A')_r C-N-CH-C-E}}$$

selectively removing the protecting group Q, whereupon cyclization occurs, and removing the protecting group P and other side-chain protecting groups from compound XXI to give a compound of the general formula II.

The invention also relates to compounds of the general formulae Va and Vb:

$$\underset{R}{\overset{L}{G-NH-(CH_2)_q-N-CH-COOH}} \quad (Va)$$

$$\underset{R}{\overset{L \quad O}{G-NH-(CH_2)_q-N-CH-C-E}} \quad (Vb)$$

wherein the substituents are as defined above. These compounds are intermediates in the processes for the preparation of the cyclized peptides of the invention.

The invention also involves processes for the preparation of the compounds Va and Vb.

According to one embodiment, compounds of general formula Va are prepared as follows:

(a) an α-halocarboxylic acid of the formula:

$$\underset{Hal-CH-COOH}{R} \quad (XXII)$$

wherein R is as defined above and Hal is chlorine, bromine or iodine, is reacted with an alkylene diamine of the formula:

$$H_2N-(CH_2)_q-NH_2 \quad (XXIII)$$

wherein q is as defined above, to give a compound of the formula:

$$\underset{H}{\overset{R}{H_2N-(CH_2)_q-N-CH-COOH}} \quad (XXIV)$$

(b) (i) reacting the compound of formula XXIV with suitable reagent containing the group G by standard methods of peptide synthesis, where G is as defined above, to give a compound of the formula:

$$\underset{H \quad H}{\overset{R}{G-N-(CH_2)_q-N-CH-COOH}} \quad (XXVI)$$

and reacting the compound of formula (XXVI) with a reagent containing L by standard methods of peptide synthesis, where L is as defined above, to give a compound of the formula Va; or (ii) reacting the compound of formula XXIV with a suitable reagent containing G by standard methods of peptide synthesis, where G as defined above to give a compound of the formula:

$$\underset{H \quad G}{\overset{R}{G-N-(CH_2)_q-N-CH-COOH}} \quad (XXVIII)$$

selectively removing the protecting group G from the secondary amino function to give a compound of the general formula XXVI.

Compounds of general formula Vb may be prepared as follows:

(i) from the compound Va thus obtained by reacting this free acid with the appropriate reagent containing the group E by standard methods of peptide synthesis, wherein E is as defined above, to give the ester, amide, or covalent bond with the polymeric support; or (ii) from compounds of the formula VIb by reacting this free amine with the appropriate reagent containing the group E by standard methods of peptide synthesis, wherein E is as defined above, to give the ester, amide, or covalent bond with the polymeric support;

The compounds of formula VIb are obtained from compound XXVI by reacting the amino acid with the appropriate reagent containing the group E as defined above and the appropriate reagent L as defined above, to give the ester, amide, or covalent bond with the polymeric support.

In the compounds of formulae V to XXVIII described above, the protecting groups G, L or J are preferably t-butyloxycarbonyl (BOC), fluorenylmethoxy carbonyl (Fmoc), or benzyloxy carbonyl (Z), and the protecting group Q is preferably, in addition to the above, benzyl (Bzl), acetamidomethyl (ACM), or tertiary butyl (t-Butyl).

In the processes described above, the coupling agents are preferably dicyclohexylcarbodiimide (DCC), bis(2-oxo-3-oxazolidinyl)phosphinic chloride (BOP-Cl), benzotriazolyl-N-oxytrisdimethylaminophosphonium hexafluoro phosphate (BOP), 1-oxo-1-chlorophospholane (Cpt-Cl), and a mixture of DCC and hydroxybenzotriazole (HOBT).

The invention also relates to pharmaceutical compositions comprising as active ingredients the cyclized peptides of the invention which may be used where selective bioaction of the peptides is required. The cyclic peptides of the invention can be used as stable and selective agonists of natural peptides, for example neuropeptides such as human tachikinins. The pharmaceutical compositions of the invention may be used for treatment of various disease states where involvement of tachikinins is implied. As such, they may be used, for example, for treatment of various inflammatory diseases, psoriasis, rheumatoid arthritis, and neurological disorders such as Familial Dysautonomia, Parkinsonism, Alzheimer's disease, and Retardive Dyskinesia. The present preparations may also be useful as analgesics. The preparations may also be used as hypotensive agents and respiratory stimulants.

The novel compositions contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate, and gums, with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral administration or for injection, the term including subcutaneous, transdermal, intravenous, intrathecal, etc. administration. The liquid compositions include aqueous solutions, flavored syrups, aqueous or oily suspensions, flavored emulsions with edible oils, as well as elixirs and similar pharmaceutical vehicles. In addition, the compositions of the present invention may be prepared as aerosols, for intra-nasal and like administration.

The active dose for humans is generally in the range of from 0.05 mg to about 50 mg per kg body weight, in regimen of 1–4 times a day. However, administration every two days or more is also possible. Specific dosages would be determined by the attending physician according to the disease to be treated, method of administration, patient's age, weight, counterindications and the like.

EXAMPLES

SYNTHESIS GENERAL—MATERIALS AND METHODS

Alkylene diamines were purchased from Merck Schuchatdt and were used without further purification. α-Chloro carboxylic acids were synthesized from the corresponding amino acids (Kopepenhoefer, B; Schurig, V. Organic Synthesis, 66, 151 (1987), Heathcock, C. H. Ed; Organic Syntyesis Inc. U.S.A.). α-Bromo carboxylic acids were prepared according to modified procedure (Kopepenhoefer, B; Schurig, V., Organic Synthesis, 66, 151 (1987), Heathcock, C. H. Ed; Organic Syntyesis Inc. U.S.A.) (5N HBr was used instead of 5N HCl). Benzyl p-nitrophenyl carbonate and BOP-Cl were purchased from Aldrich. BOP-Cl was purified according to the known procedure (Van Der Awers, C. and Anteumis, M. J. O. Int. J. Peptide Protein Res. 29, 574 (1987)). BOP reagent was purchased from Richelieu Canada. Thionyl chloride was refluxed and distilled over flax oil. All solvents were analytically pure and used without further purification. HPLC was performed on a Merck Hitachi 655A equipped with a LC-5000 gradient pump and UV-VIS detector with tunable wave length set at 220 nm. The flow was fixed at 1 mL/min and the eluants were water (+0.05% TFA), MeOH and MeCN. The reverse phase silica columns were LICHROSPHERE RP-18 or RP-8 15 cm×4.2 mm ID from Merck. Optical purity was checked on CHIRASPHER$^R$, a chiral separation column from Merck (5µ, 25 cm×4 mm ID). The flow was fixed at 1 mL/min and the eluant was a mixture of n-hexane-dioxane-i-propanol 50/44/5. The detector was set to 254 nm. Melting points were measured on a Thomas Hoover capillary machine and optical activity was measured on a Perkin Elmer-model 141 polarimeter in a 10 cm length cell with a sodium lamp at 25° C. Microanalysis was carried out at the microanalytical department of The Hebrew University, Jerusalem. $^1$H NMR spectra of building units and dipeptides were recorded on a BRUKER WP-200 pulsed FT spectrometer. Samples were dissolved in CDCl$_3$. Chemical shifts are in ppm relative to TMS internal standard. $^1$H NMR spectra of peptide Ib were recorded on BRUKER AMX-500 and 600 spectrometers, operating at 500 and 600 MHz proton resonance frequencies. Data were processed on BRUKER X32 work station using the UXNMR program. 31 mg of peptide were dissolved in DMSO-d$_6$ from Aldrich in a 5 mm NMR tube. Spectra were recorded at 303K. The assignment of the proton resonances was carried out following standard procedures (Wutrich, K., NMR of Proteins and Nucleic Acids, John Wiley, NY, 1986) using the homonuclear NOESY, ROESY, TOCSY AND E. COSY techniques. FAB-MS was determined on a ZAB-3HF FAB/tandem mass spectrometer or on an APIII LC/MS/MS.

SYNTHESIS OF BUILDING UNITS AND DIPEPTIDES

Method A

Preparation of N-(ω-amino alkylene) amino acids.

The appropriate alkylene diamine (15.8 mol) was rapidly stirred at 4° C. (if the alkylene diamine is solid it was dissolved in 500 mL CH$_2$Cl$_2$) while the α-halogeno carboxylic acid (1.6 mol) was added portionwise ensuring that each addition had solubilized. The reaction was then stirred at 25° C. for 48 h and evaporated in vacuo (60° C.).

To the resulting paste, a solution of DMSO/Ether/Ethanol (3:1:1) 500 mL was added and the mixture left overnight in the freezer. The precipitated zwitterions were collected by filtration on sintered glass and washed with ethanol and ether. In some cases the products were obtained as the dihydrochloride salts rather than the zwitterions (structures and chemical data see Table I). The optical purity of compounds 6 and 7 was checked on their fully protected derivatives 14 and 15 (see method C and Table II).

Method B

Selective protection of N-(ω-amino alkylene) amino acids.

A solution of benzyl p-nitrophenyl carbonate (0.605 mol) in dioxane (1.3 L) was added dropwise to a stirred solution of the N-(ω-amino alkylene) amino acid (0.4 mol) in 50% aqueous dioxane (2.6 L). The mixture was maintained at pH=11 (with 2N NaOH in an automatic titrator). After stirring for 24 h at room temperature the mixture was evaporated to dryness, dissolved in H$_2$O (1.2 L) and filtered. The filtrate was extracted with EtOAc (2×1 L) and the aqueous layer was cooled in a water-ice bath and acidified to pH=5.5 with 6N HCl. After extraction with ether (2×1 L), the aqueous layer was acidified (pH=1 with concentrated HCl), evaporated to dryness and reevaporated from i-PrOH. Isopropyl alcohol. In one case (starting material 1 Table I) crystallization from i-PrOH gave the acid 8 (Table II). When this procedure was applied to materials 2–7 the products were oils or were obtained in low yield. In these cases the crude mono protected N-(Z-ω-amino alkylene) amino acids were esterified according to method C below. This procedure increased considerably the overall yields of the diprotected N-(ω-amino alkylene) amino acids. Alternatively, the crude mono protected N-(ω-amino alkylene) amino acids could be protected on the $N^\alpha$ with Boc (method H below), then the $N^\omega$-Z cleaved (method K below) and the $N^\omega$ protected with Fmoc (method J) (structures and chemical data see Table II)

Method C

Esterification of mono protected N-(ω-amino alkylene) amino acids.

Crude N-(Z-ω-amino alkylene) amino acids (40 mmol) were suspended and stirred in anhydrous MeOH (600 mL) and dry HCl ($H_2SO_4$ trap) was bubbled for 1 h. The stirring was continued for 1 h at room temperature and the MeOH was evaporated in vacuo.

The crude product was dissolved in water (500 mL) and washed with EtOAc (2×500 mL). The pH of the water was raised to 8 (saturated $NaHCO_3$) and extracted with EtOAc (3×300 mL). The organic phase was dried over $MgSO_4$ and evaporated to dryness in vacuo. (structures and chemical data see Tables II and III). The optical purity of the two enantiomers 14 and 15 was checked on CHIRASPHER$^R$ column. Each compound gave only one peak at different k' whereas a mixture gave two peaks with the same k's corresponding to those of the pure compounds.

Method D

Preparation of N-(ω-Boc-amino alkylene) Gly.

1. Preparation of Boc-alkylene diamine.

The appropriate alkylene diamine (1 mol) was dissolved in $CHCl_3$ (1 L). The stirred solution was cooled in an ice bath and $(Boc)_2O$ (0.1 mol in 0.5 L $CHCl_3$) was added dropwise. The solution was stirred additional 24 h at room temperature and the solvent evaporated to dryness in vacuo. The resulting oil was dissolved in ether (0.5 L) and washed with brine (6×200 mL). The etheral layer was dried on $MgSO_4$ and evaporated to dryness in vacuo. The resulting oil was dried on $P_2O_5$ in vacuo.

2. The appropriate Eeono Boc-alkylene diamine (1 mol) was rapidly stirred at 0° C. while 2-chloro acetic acid (0.1 mol) was added portionwise ensuring that each addition had solubilized. The mixture was left overnight at room temperature, then ether was added (50 mL) and the precipitate collected by filtration, washed with ether (3×50 mL) and dried over $P_2O_5$. The solid dissolved in water (pH=10) and lyophilized. The solid was dissolved in water (80 mL) and the $N^\alpha$ protected with Fmoc (method J) to give products 16 & 17 (see Tables II and III).

Method E

Selective deprotection of Z—N—(Z-ω-amino alkylene) amino acids.

N-(ω-amino alkylene) amino acids were reacted with 2 equivalents of Z-Cl according to method L. The di-Z products (30 mmol) were dissolved in neat $SOCl_2$ (50 mL) and warmed to 60° C. for 0.5 h. The solution was evaporated in vacuo and HCl 2N (100 mL) was added to the resulting paste. The mixture was stirred for 3 h and washed with ether (3×100 mL). The pH of the solution was adjusted to 9 and the $N^\alpha$ amino group protected with Boc in situ (method H). The $N^\omega$ Z-protecting group was removed by catalytic hydrogenation (method K) and reprotected with Fmoc (method J) (see Tables II and III). Alternately, MeOH was added to the paste instead of HCl to give, after evaporation in vacuo, esters 9–15 (scheme 2 and table II).

Method F

Coupling with BOP-Cl.

BOP-Cl (1.1 mmol) was added to a stirred solution of the diprotected N-(ω-amino alkylene) amino acids (1 mmol) followed by 1.2 mmol of DIEA in 10 mL MeCN at −15° C. The solution was stirred for 20 min at −15° C. and the amino acid ester salt (1 mmol) was added in 210 mL of MeCN with 1.1 mmol of DIEA. The stirring was continued overnight at 0° C. The solvent was evaporated under vacuo and the crude product dissolved in EtOAc and washed with saturated solutions of $KHSO_4$ (2×300 mL), $NaHCO_3$ (2×300 mL) and brine (2×300 mL). The organic phase was dried over $MgSO_4$ and evaporated in vacuo to dryness. (see Table IV)

Method G

Coupling with BOP.

To a stirred solution of the amino acid ester component (1 mmol) in $CH_2Cl_2$ (10 mL) were added BOP reagent (1.1 mmol) and the diprotected N-(ω-amino alkylene) amino acids (1.1 mmol) and DIEA (3 mmol) at room temperature. After 15 min the pH was checked for basicity (in cases where the pH was lower than pH=9, more DIEA was added) and the reaction mixture left for 1 h at room temperature. The solvent was evaporated under vacuum and the crude product dissolved in EtOAc (100 mL) and washed as described in method F above (see Table IV).

Method H

Preparation of Boc-amino acids (Nagasawa et al., Bull. Chem. Soc. Jap., 46, 1269 (1973)).

Amino acid (0.1 mol) was dissolved in NaOH (1N, 200 mL) and dioxane (200 mL) added. The mixture was stirred in an ice bath and a solution of $(Boc)_2O$ (0.14 mol) in dioxane (200 mL) was added dropwise while the pH was maintained at 9. The mixture was left stirring at room temperature over night. The dioxane was evaporated in vacuo and the water solution washed with ether (3×150 mL), cooled and acidified with saturated $KHSO_4$ solution to pH 3. The precipitate was collected by filtration, washed with cold water and dried on $P_2O_5$ in vacuo to constant weight. If upon acidification an oil was formed, it was extracted with EtOAc (3×150 mL) which was washed with saturated NaCl, dried over $MgSO_4$ and evaporated to dryness. After drying over $P_2O_5$, the residue was crystallized from EtOAc/petrol ether.

Method J

Preparation of Fmoc-amino acids (Sivanandaiah, K. M.; Rangaragn, M. S., Ind. J. Chem., 25(B), 1045 (1986)).

A solution of Fmoc-OSu (0.024 mol) in MeCN (25 mL) was added at once to a stirred aqueous solution of amino acid (0.025 mol) adjusted to pH 9 with TEA. The pH was maintained at 8.5–9 with TEA. After 15 min the pH stabilized and the reaction mixture was left another 15 min. The MeCN was evaporated in vacuo, the pH adjusted to 3 with saturated $KHSO_4$ and the precipitate collected by filtration, washed with cold water and dried over $P_2O_5$ to constant weight. If upon acidification an oil formed it was treated as in method H.

Method K

Removal of the Z protecting group (Anwer, M. K.; Spatola, A. F., Synthesis, 929 (1980)).

To a solution of Z-amino acid (1 gr) dissolved in MeOH (5 mL), Pd/C 10% (0.1 gr) and ammonium formate (1 gr) were added with stirring. The advance of the reaction was followed by HPLC. After completion (~2 h), the catalyst was removed by filtration and the filtrate evaporated to dryness in vacuo. The residue was dissolved in water which were lyophilized.

Method L

Preparation of Z-amino acids (Bergman, M.; Zervas, L., Bet. 65, 1192 (1932)).

Z-amino acids were prepared according to method H, but Z-Cl was used instead of $(Boc)_2O$.

TABLE I

Data for compounds of structure (Va) (G = H; L = H)

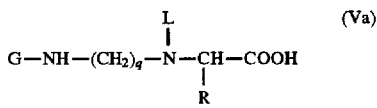

(Va)

| serial no. | q= | R | method | % yield | mp, °C. | anal. (d) | $(\alpha)_D^{19}$ |
|---|---|---|---|---|---|---|---|
| 1 | 2 | H | A | 72 | 153 | C,H,N | — |
| 2 | 3 | H | A | 69(a) | 153 | C,H,N,Cl | — |
| 3 | 6 | H | A | 53(a) | 202 | C,H,N,Cl | — |
| 4 | 2 | Me | A | 41(a) | 198 | C,H,N | D,L |
| 5 | 6 | Me | A | 47(a) | 204 | C,H,N | D,L |
| 6 | 2 | i-Bu | A | 36 | 211 | C,H,N | −24,4(b) |
| 7 | 2 | i-Bu | A | 37 | 209 | C,H,N | 26(c) |

(a)as dihydrochloride (b)D enantiomer, c 0.3, 6N HCl (c)L enantiomer, c 0.32, 6N HCl (d)C,H,N indicate that the experimental fits the calculated analysis within 0.3% error.

TABLE II

Data for compounds of structure (Vb)

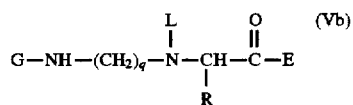

(Vb)

| serial no. | q = R | R | E | G | L | method | % yield | k'(a) | anal. (g) | $[\alpha]_D^{19}$(b) |
|---|---|---|---|---|---|---|---|---|---|---|
| 8 | 2 | H | OH | Z | H | B | 37(c) | — | C,H,N,Cl | — |
| 9 | 2 | H | OMe | Z | H | B,C | 48 | 1.02 | C,H,N | — |
| 10 | 3 | H | OMe | Z | H | B,C | 34 | 1.08 | C,H,N | — |
| 11 | 6 | H | OMe | Z | H | B,C | 23 | 1.15 | C,H,N | — |
| 12 | 2 | Me | OMe | Z | H | B,C | 19 | 1.15 | c,H,N | D,L |
| 13 | 6 | Me | OMe | Z | H | B,C | 28 | 1.23 | C,H,N | D,L |
| 14 | 2 | i-Bu | OMe | Z | H | B,C | 31(d) | 1.26 | C,H,N | 7.27(e) |
| 15 | 2 | i-Bu | OMe | Z | H | B,C | 29 | 1.3 | C,H,N | −7.1(f) |
| 16 | 3 | H | OH | BOC | FMOC | D | 33 | 1.12 | C,H,N | — |
| 17 | 6 | H | OH | BOC | FMOC | D | 26 | 1.26 | C,H,N | — |
| 18 | 3 | i-Bu | OH | Z | BOC | E | 43 | — | C,H,N | −5.8 |
| 19 | 2 | H | OH | FMOC | BOC | E | 42 | 1.08 | C,H,N | — |
| 20 | 2 | H | OH | FMOC | BOC | B | 85 | 1.08 | C,H,N | — |
| 21 | 3 | i-Bu | OH | FMOC | BOC | E | 94 | 1.3 | C,H,N | −7.3 |

(a)RP-18 column, 70% MeOh (b)c 1, MeOH (c)as hydrochloride
(d)include ½ H₂O (e)D enantiomer (f)L enantiomer
(g)C,H,N indicate that the experimental analysis fits the calculated values within 0.3% error.

TABLE III

¹H NMR data on compounds 9-21

| Compound | ¹H NMR |
|---|---|
| 9 | 7.4(5H, Ar), 5.6(1H, Amide), 5.08(2H, Bz), 3.7(3H, s, O—CH₃), 3.4(2H, s, N—CH₂—CO), 3.25(2H, m, CH₂), 2.75(2H, t, CH₂), 1.8(1H, s, Amine). |
| 10 | 7.35(5H, Ar), 5.75(1H, Amide), 5.08(2H, s, Bz), 3.07(3H, s, O—CH₃), 3.35(2H, s, N—CH₂—CO), 3.25(2H, m, N—CH₂), 2.6(2H, t, N—CH₂), 1.8(1H, s, Amine). |
| 11 | 7.35(5H, Ar), 5.35(1H, Amide), 5.08(2H, s, Bz), 3.7(3H, s, O—CH₃), 3.35(2H, s, N—CH₂—CO), 3.15(2H, m, N—CH₂), 2.5(2H, m, N—CH₂), 1.85(1H, s, Amine), 1.45(4H, m, N—CH₂—CH₂—CH₂—CH₂—CH₂—CH₂—N), 1.3(4H, m, CH₂—CH₂). |

TABLE III-continued

¹H NMR data on compounds 9-21

| Compound | ¹H NMR |
|---|---|
| 12 | 7.35(5H, Ar), 5.4(1H, Amide), 5.1(2H, Bz), 3.7(3H, s, O—CH$_3$), 3.35(2H, m, N—CH$_2$), 3.22(1H, m, αH), 2.6-2.8(2H, m, N—CH$_2$), 1.85(1H, s, Amine), 1.28(3H, d, CH$_3$). |
| 13 | 7.35(5H, Ar), 5.3(1H, Amide), 5.1(2H, s, Bz), 3.7(3H, s, O—CH$_3$), 3.35(1H, m, αH), 3.15(2H, q, N—CH$_2$), 2.5(2H, m, N—CH$_2$), 1.85(1H, s, Amine), 1.5(4H, m, N—CH$_2$—CH$_2$—CH$_2$—CH$_2$—CH$_2$—CH$_2$—N), 1.28(7H, m, CH$_3$, CH$_2$—CH$_2$). |
| 14, 15 | 7.35(5H, Ar), 5.5(1H, Amide), 5.1(2H, s, Bz), 3.7(3H, s, O—CH$_3$), 3.35(2H, m, N—CH$_2$), 3.20(H, m, αH), 2.7(2H, m, N—CH$_2$), 1.9(1H, s, Amine), 1.49(2H, m, CH$_2$), 1.45(1H, m, CH$_2$—CH(CH$_3$)$_2$), 0.9(6H, d, CH$_2$—CH(CH$_3$)$_2$). |
| 16 | 7.7(2H, Ar), 7.6(2H, Ar), 7.2-7.4(4H, Ar), 4.4-4.7(2H, m, Bz), 4.2(1H, m, Fluorenyl-CH), 3.8 (2H, m, CH$_2$), 2.7-3.5(4H, m, N—CH$_2$—CH$_2$—CH$_2$—N), 1.45(11H, s, CH$_2$ + Boc). |
| 17 | 7.7(2H, Ar), 7.6(2H, Ar), 7.2-7.4(4H, Ar), 3-4.6(9H, Fluorenyl-CH$_2$, CH$_2$CO, 2xCH$_2$—N, Bz), 1-1.5(13H, s, CH$_2$—CH$_2$ + Boc). |
| 18 | 7.45(5H, Ar), 6.0(1H, NH), 5.2(2H, m, Bz), 3.3-3.9(5H, αH, CH$_2$—CH$_2$—CH$_2$), 1.6-2.0(5H, CH—CH$_2$, CH$_2$—CH$_2$—CH$_2$, 1.43(9H, Boc). |
| 19, 20 | 7.7(2H, Ar), 7.6(2H, Ar), 7.2-7.4(4H, Ar), 4.4-4.7(2H, m, Bz), 4.2(1H, m, Fluorenyl-CH), 3.8 (2H, m, N—CH$_2$), 2.7-3.5(4H, m, CH$_2$—CH$_2$, 1.45(9H, Boc). |
| 21 | 7.8(2H, Ar), 7.6(2H, Ar), 7.2-7.4(4H, Ar), 4.1-4.4(4H, CHCO, CH$_2$, 3-3.4 (4H, 2xCH$_2$—N), 1.5-2(4H, 2xCH$_2$), 1.45(9H, Boc), 0.9(6H, d, CH$_2$—CH(CH$_3$)$_2$). |

TABLE IV

Data for compounds of structure VIIIb (E = OMe; n = 1; G = Z; J = Boc)

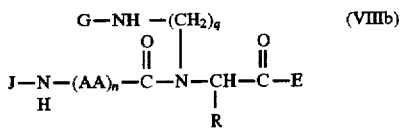

(VIIIb)

| serial no. | AA | R | q= | method | % yield | (MH)⁺ Calc | Found | k'(a) | anal. | (α)$_D$¹⁹(b) |
|---|---|---|---|---|---|---|---|---|---|---|
| 22 | Phe | H | 2 | F | 87 | 514 | 514 | 1.35 | C,H,N | -3.43 |
| 23 | Leu | H | 2 | F | 98 | 480 | 480 | 1.48 | C,H,N | — |
| 24 | Trp (For) | H | 2 | F | 98 | 581 | 581 | 1.6 | C,H,N | -8.73 |
| 25 | Phe | Me | 2 | G | 98 | 528 | 528 | 2.16(c) | C,H,N | 4.43 |
| 26 | Phe | i-Bu | 2 | F | 95 | 570 | 570 | 2.1(c) | C,H,N | 3.4 |
| 27 | Phe | H | 3 | F | 97 | 528 | 528 | 1.63 | C,H,N | 0.0 |
| 28 | Phe | Me | 6 | G | 99 | 584 | 584 | 2.4(c) | C,H,N | -4.52 |
| 29 | Phe | H | 6 | G | 96 | 570 | 570 | 1.82 | C,H,N | -4.58 |

(a)RP-18 column. 80% MeOH (b)c 1. MeOH (c)RP-18 column. 75% MeOH

PEPTIDE SYNTHESIS

A preferred method for the preparation of the peptides of this invention is according to the Solid Phase Peptide Synthesis methodology using a combination of Boc and Fmoc chemistries (e.g. Bodanszky, "Principles of Peptide Synthesis", Springer-Verlag, 1984; or Bodanszky et al., "the Practice of Peptide Synthesis", Springer-Verlag, 1984; or Barany and Merrifield, in "The Peptides: Analysis, Synthesis and Biology", Vol. 2, Chapter 1, Academic Press, 1980; or Atherton et al., Bioorg. Chem., 8, 1979). In the process of the present invention a preferred p-methyl benzhydrylamine polystyrene 1% divinyl benzene polymer (MBHA resin, degree of substitution was 0.9 eq. NH$_2$/gr., 1 gr (0.9 mmol)) was coupled with 2.4 mmol Boc-Met. The coupling was performed with BOP (2.4 mmol) and DIEA (5.6 mmol) in DMF. After 3 h the resin was reacted with Ac$_2$O (8 mmol) and DMAP (0.5 mmol) for 3 h and the resin washed 5 times with DCM.

Method M
Boc Solid Phase Synthesis

Each synthetic cycle consisted of (i) a 1 min. followed by 20 min deprotection with TFA:DCM (1:2) (ii) 5 DCM washes (iii) 2×5 min neutralization with 5% DIEA in DMF (iv) 5 DMF washes (v) 60 min coupling with 2.4 mmol Boc-AA using BOP (2.4 mmol) and DIEA (5.6 mmol) in DMF (vi) checking for completion by the Kaiser test (Kaiser, E., et al., Anal. Biochem. 34, 595 (1970)) (vii) 5 DCM washes.

Method N
Fmoc Solid Phase Synthesis

Each synthetic cycle consisted of (i) a 17 min deprotection with 20% piperidine in DMF (ii) 6 DMF washes (iii) 60 min coupling with 2.4 mmol Fmoc-AA using BOP (2.4 mmol) and DIEA (5.6 mmol) in DMF (iv) 6 DMF washes, and (v) Kaiser test.

Side-chain protection: Arg(Tos); Asp(OBzl); N(mercaptopropylene)Gly(SBzl); 5-mercapto valeric acid (SBzl); N(γ-Boc aminopropylene)Gly.

Method P

Removal of the Peptide from the Resin and Subsequent Removal of Protecting Groups In a KEL-F vessel were put: 1 gr resin, magnetic stirrer and 2 mL anisole. The vessel was attached to the HF rector (Type I made by the Peptide Institute Inc. Osaka, Japan).

Synthesis of Peptide Ic

Peptide Ic was synthesized according to the following scheme using general methods M, N, P and Q.

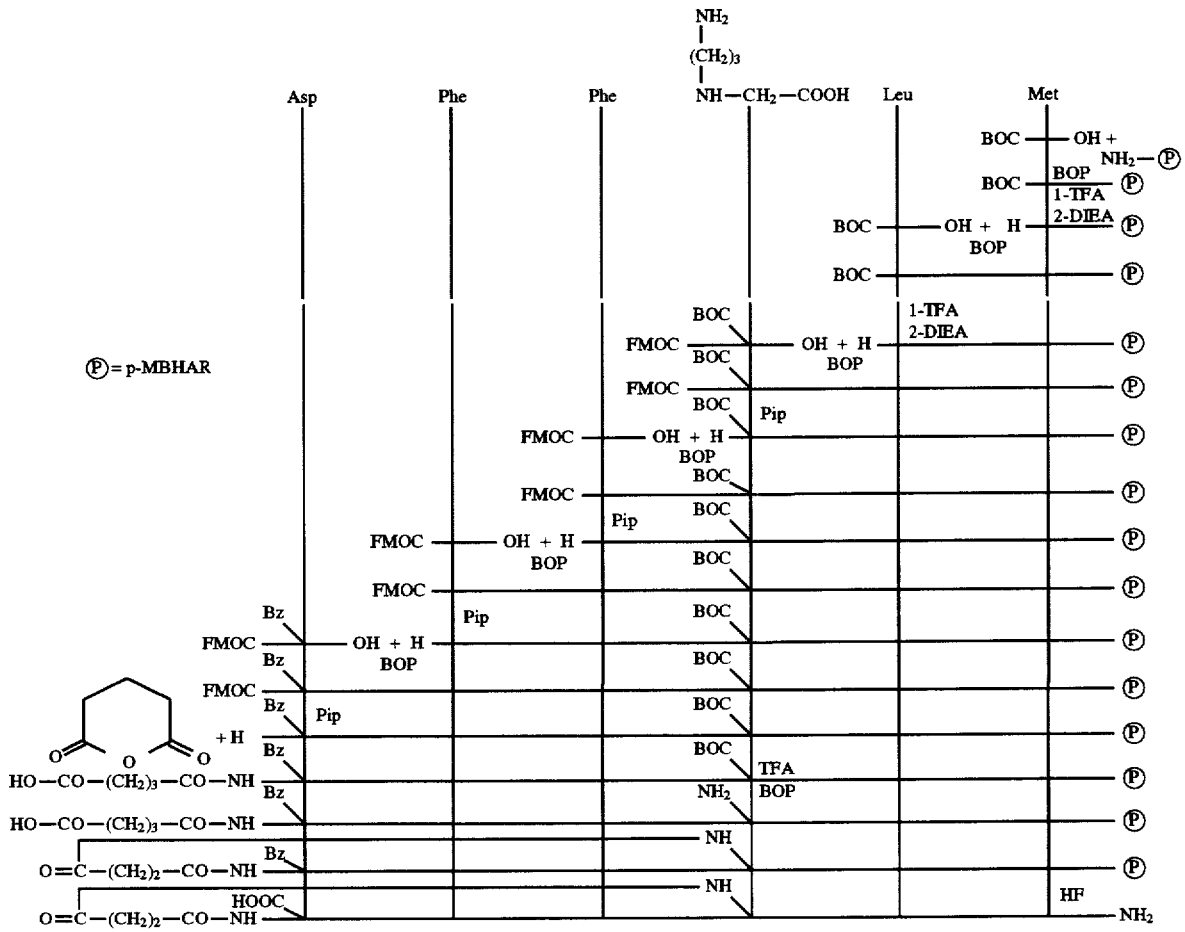

After removal of air by vacuum, the reaction vessel was frozen by liquid nitrogen and charged with 20 ml liquid HF. The vessel was kept for 1.5 h at −7° C. with stirring. HF was evaporated to dryness and hexane (50 mL) was added to the reaction vessel. After mixing, the hexane was decanted and the reaction mixture was washed with ether (3×50 mL) which was decanted. The mixture was treated with 30% AcOH (3×50 mL) and filtered on a sintered glass funnel. The solvent was lyophilized. The yields of the crude peptides was 50–80%.

Method O

On Resin Cyclization of Peptides Ia–Ic

After the main chain was synthesized, the Boc protecting group was removed from N(γ-aminopropylene)Gly by TFA and the resin washed and neutralized as described for Boc Solid Phase Synthesis (i)–(iv). Cyclization (Felix, A. M., et al., in "Peptides" Marshall, G. B., Ed. p. 465 (1988)) was performed with BOP (2.4 mmol) an DIEA (3.6 mmol) for 24 h. After 24 h, if the Kaiser test was negative, the resin was washed with MeOH and dried in vacuo over $P_2O_5$. If the Kaiser test was positive, another portion of BOP (1.2 mmol) and DIEA (1.8 mmol) were added. After the cyclization peptides were removed from the resin as described above.

The crude peptide was purified by semiprep HPLC on a HIBAR RP-8 column with a gradient of A=$H_2O$ (0.1% TFA); B=MeCN (0.1% TFA). t=0, A=70, B=30; t=10, A=70, B=30; t=50, A=20, B=80; t=60, A=0, B=100; $R_t$=20.3 min. MW+=880.06; FAB-MS found $(MH)^+$=881.14; API-MS found (MH)+=881.60; AAA found Asp=0.9; Phe=1.95; Met=0.95; Leu=1.0.

Synthesis of Peptide Ia

Peptide Ia was synthesized according to the scheme of peptide Ic above using general methods M, N, P and Q. Instead of Fmoc-Asp(OBzl), Fmoc-Arg(Tos) was coupled and instead of glutaric anhydride the peptide was reacted with adipic acid.

The crude peptide was purified by semiprep HPLC on a HIBAR RP-8 column with a gradient of A=$H_2O$ (0.1% TFA); B=MeCN (0.1% TFA). t=0, A=70, B=30; t=5, A=70, B=30; t=30, A=0, B=100; $R_t$=23.9 min.

MW=936.1; FAB-MS found $(MH)^+$=937; API-MS found $(MH)^+$=937.1; AAA found Arg=0.8; Phe=1.95; Met=0.95; Leu=1.0.

Synthesis of Peptide Ib

Peptide Ib was synthesized according to the scheme of peptide Ic above using general methods M, N, P and Q.

Instead of Fmoc-Asp(OBzl), Fmoc-Arg(Tos) was coupled. The crude peptide was purified by semiprep HPLC on a HIBAR RP-8 column with a gradient of A=H2O (0.1% TFA); B=MeCN (0.1% TFA). t=0, A=60, B=40; t=10, A=60, B=40; t=40, A=20, B=80; t=50, A=0, B=100; $R_t$=24 min.

MW=962.25; FAB-MS found (MH)+=963.1; API-MS found (MH)+=963.2; AAA found Arg=0.9; Phe=2.05; Met=0.85; Leu=0.95. Proton NMRpeak assignment is shown in Table V.

Synthesis of Peptide Id

Peptide Id was synthesized according to the scheme of peptide Ic above using general methods M, N, P and Q. Instead of Fmoc-Asp(OBzl), Fmoc-Arg(Tos) was coupled. Instead of Fmoc-N(g-Boc-amino propylene)Gly, Fmoc-N(g-mercapto(SBzl)propylene)Gly was used and instead of glutaric anhydride, d-mercapto(SBzl)valeric acid was used.

Cyclization of Peptide Id

Peptide Id was removed from the resin by HF to yield the reduced form. After lyophilization the crude peptide dissolved in MeOH (1 L) and $I_2$ (0.8 mmol) was added. The solution was kept at room temperature for 72 h with stirring. The progress of the oxidation reaction was followed by HPLC. Residual SH groups were determined by the Ellman test (Ellman, G. L., Biochem. Biophys. 82, 70 (1959)). After completion, the solvent was evaporated in vacuo and the peptide was purified by preparative HPLC.

Table V.

Proton chemical shifts of peptide Ib in DMSO at 303K.[a]

[a] The chemical shifts of the minor isomer (accounting for 18%) with a cis configuration of the Phe[3]-NGly[4] peptide bond are given in parentheses. The prochiral assignments of the β-protons of the Phe residues is given.

| Residue | NH | C$^\alpha$H | C$^\beta$H | C$^\gamma$H | C$^\delta$H | other |
|---|---|---|---|---|---|---|
| Arg[1] | 8.13 | 3.92 | 1.58 | 1.33 | 3.01 | C$^\epsilon$H 7.47 |
|  |  |  | 1.44 | 1.28 |  |  |
|  | (7.87) | (4.01) | (1.54) | (1.31) | (2.98) | (7.44) |
|  |  |  | (1.40) | (1.20) |  |  |
| Phe[2] | 7.08 | 4.55 | 3.02 R |  |  | aromatic |
|  |  |  | 2.77 S |  |  | 7.12–7.29 |
|  | (7.34) | (4.41) | (3.03 S) |  |  | (7.12–7.29) |
|  |  |  | (2.82 R) |  |  |  |
| Phe[3] | 9.02 | 4.92 | 3.04 S |  |  | aromatic |
|  |  |  | 2.79 R |  |  | 7.12–7.29 |
|  | (8.35) | (4.58) | (3.16 S) |  |  | (7.12–7.29) |
|  |  |  | (2.80 R) |  |  |  |
| NGly[4] |  | 3.99 |  |  |  |  |
|  |  | 3.76 |  |  |  |  |
|  |  | (4.51) |  |  |  |  |
|  |  | (3.91) |  |  |  |  |
| Leu[5] | 8.01 | 4.26 | 1.48 | 1.65 | 0.89 |  |
|  |  |  | 1.43 |  | 0.85 |  |
|  | (8.43) | (4.37) | (1.47) | (1.63) | (0.89) |  |
|  |  |  | (1.43) |  | (0.86) |  |
| Met[6] | 7.92 | 4.24 | 1.94 | 2.46 |  | C$^\epsilon$H$_3$ 2.01 |
|  |  |  | 1.83 | 2.37 |  |  |
|  | (8.08) | (4.23) | (1.80) | (2.38) |  | (2.01) |
|  |  |  | (1.72) | (2.28) |  |  |
| I |  | 2.28 | 1.76 | 2.08 |  |  |
|  |  | 2.03 | 1.73 | 1.97 |  |  |
|  |  | (2.23) | (1.78) | (2.08) |  |  |
|  |  | (2.08) | (1.70) | (1.98) |  |  |
| II | 7.56 | 2.97 | 1.52 | 3.33 |  |  |
|  |  |  | 1.45 |  |  |  |
|  | (7.31) | (3.26) | (1.71) | (3.82) |  |  |
|  |  | (2.91) | (1.62) | (2.85) |  |  |
| NH$_2$ | 7.24, 7.04 |  |  |  |  |  |
|  | (7.16, |  |  |  |  |  |
|  | 7.01) |  |  |  |  |  |

Synthesis of Peptide IIa

Peptide IIa was synthesized according to the scheme of peptide Ic above using general methods M, N, P and Q. Instead of Boc-Met, Boc-Hcys(SBzl) was coupled to the PMBHA resin. Instead of Fmoc-Asp(OBzl), Fmoc-Arg(Tos) was coupled and instead of glutaric anhydride the peptide was reacted with acetic anhydride.

Cyclization of Peptide IIa

Peptide IIa was removed from the resin in the reduced form. After lyophilization the crude peptide was dissolved in a saturated NH$_3$/MeOH solution (1 L) at 0° C. The solution was kept at room temperature for 72 h with stirring. The progress of the reaction was followed by HPLC. Residual SH groups were determined by the Ellman test (Ellman, G. L., Biochem. Biophys. 82, 70 (1959)). After completion, the solvent was evaporated in vacuo and the peptide was purified by semi-preparative HPLC on a RP-18 HIBAR column with a gradient of A=H$_2$O (0.1% TFA); B=MeCN (0.1% TFA). t=0, A=60, B=40; t=10, A=60, B=40; t=40, A=20, B=80; t=50, A=0, B=100; $R_t$=25 min.

MW=893.7; FAB-MS found (MH)+=894.9; API-MS found (MH)+=894.8; AAA found Arg=0.9; Phe=1.95; Hcys=0.75; Leu=1.0

Synthesis of Peptide IIIb

Peptide IIIb was synthesized according to the following scheme using general methods M, N and P. The crude peptide was purified by semi-preparative HPLC on a HIBAR RP-8 column with a gradient of A=H$_2$O (0.1% TFA); B=MeCN (0.1% TFA). t=0, A=70, B=30; t=5, A=70, B=30; t=40, A=20, B=80; t=50, A=0, B=100; $R_t$=22.7 min.

MW=995.3; FAB-MS found (M)+=995.4; API-MS found (MH)+=996.0; AAA found Arg=1.0; Phe=2.0; Met=0.8; Leu=0.95.

Synthesis of Peptide IIIa

Peptide IIIa was synthesized according to the scheme of peptide IIIb above using general methods M, N and P. Instead of glutaric anhydride the peptide was reacted with acetic anhydride. After acetylation the peptide was removed from the resin by HF.

The crude peptide was purified by semi-preparative HPLC on a HIBAR RP-18 column with a gradient of A=H2O (0.1% TFA); B=MeOH (0.1% TFA). t=0, A=60, B=40; t=30, A=0, B=100; $R_t$=24 min.

MW=854.5; FAB-MS found (MH)+=855.6; API-MS found (MH)+=855.6; AAA found Arg=0.8; Phe=1.95; Met=0.85; Leu=0.95

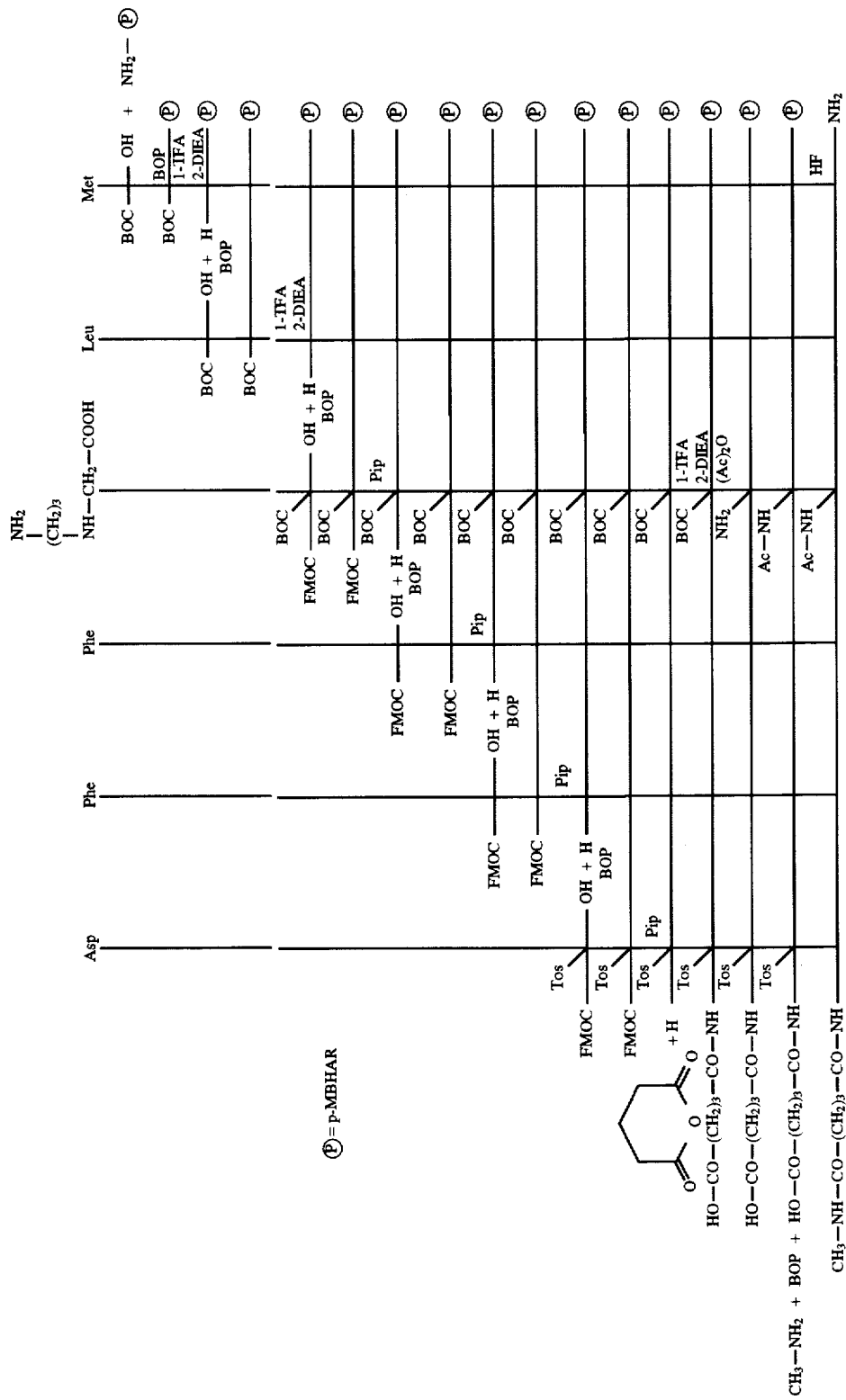

BIOLOGICAL ACTIVITY EXAMPLES

General

The biological activity of the cyclic (and comparative linear) peptides was assayed in different smooth muscle systems: Rat Vas Deferens (RVD), Guinea Pig Ileum (GPI), and Rat Portal Vein (RPV).

Assay of the activity of the different analogs in these systems enables the determination of their selectivity towards tachykinin receptors present in these tissues, namely NK-1 and NK-3 receptors in GPI, NK-3 in RPV and NK-2 in RVD. The presence of two tachykinin receptors in the GPI system prevents direct and selective assay of each one of them separately, and therefore one receptor had to be blocked when assaying the activity of the analog towards the second receptor. Blocking the NK-3 receptor in the GPI system by blocking the acetylcholine receptors with atropine enabled assaying the NK-1 receptor separately.

Methods

Assay of the resistance of the analog peptides to digestion by proteases was performed by incubating the peptide with slices, homogenates or membranes of various tissues such as brain, liver, kidney, parotid gland, etc., and assaying the residual activity after incubation, by the GPI assay.

(a) Guinea Pig Ileum Assay (GPI)

Assay was performed according to the procedures described in Wormser, U., et al., EMBO J. 5, 2805 (1986).

(b) Rat Vas Deferens Assay (RVD)

Assay was performed according to the procedure described in Chorev et al., Eur. J. Pharmacol., 127, 187 (1986).

(c) Rat Portal Vein Assay (RPV)

Rat was sacrificed by decapitation. The abdomen was cut open and all internal organs moved to the side. The portal vein was tied at both ends while within the animal and cleaned from all surrounding tissues, to obtain a clean tissue. The cleaned tissue was immersed in a bath containing Tirode's solution, aerated with a mixture of $CO_2:O_2(95:5\%)$. One of the tied ends was attached to a glass hook and the other end to a transducer lever, in order to measure the contractions. Tension was about 0.5 g. The tissue was left in the bath at 37° C. for an hour, then the peptides were added at 20 min intervals, to prevent desensitization of the receptor.

(d) Resistance to digestion by proteases

Assay was performed according to the procedures described in Chorev et al., Eur. J. Pharmacol., 127, 187 (1986).

The following specific examples demonstrate the activity of the peptides Ia, Ib, Ic, Id and IIa, some in comparison with the linear, prior art WS septide.

A. Biological activity of cyclized peptides

|  | Biological Activity ($EC_{50}$ (nM)) | | |
|---|---|---|---|
| Peptide | NK-1 | NK-2 | NK-3 |
| Ib | 11 | >50,000 | >100,000 |
| Ia | 5 | >50,000 | >100,000 |
| Ic | 15 | >100,000 | >50,000 |
| IIa20 | 20 | >100,000 | >100,000 |
| WS septide | 3 | >200,000 | >100,000 |

All of the analogs were highly selective to the NK-1 sub-receptor, as the prior art linear analog WS septide.

Figure 3:
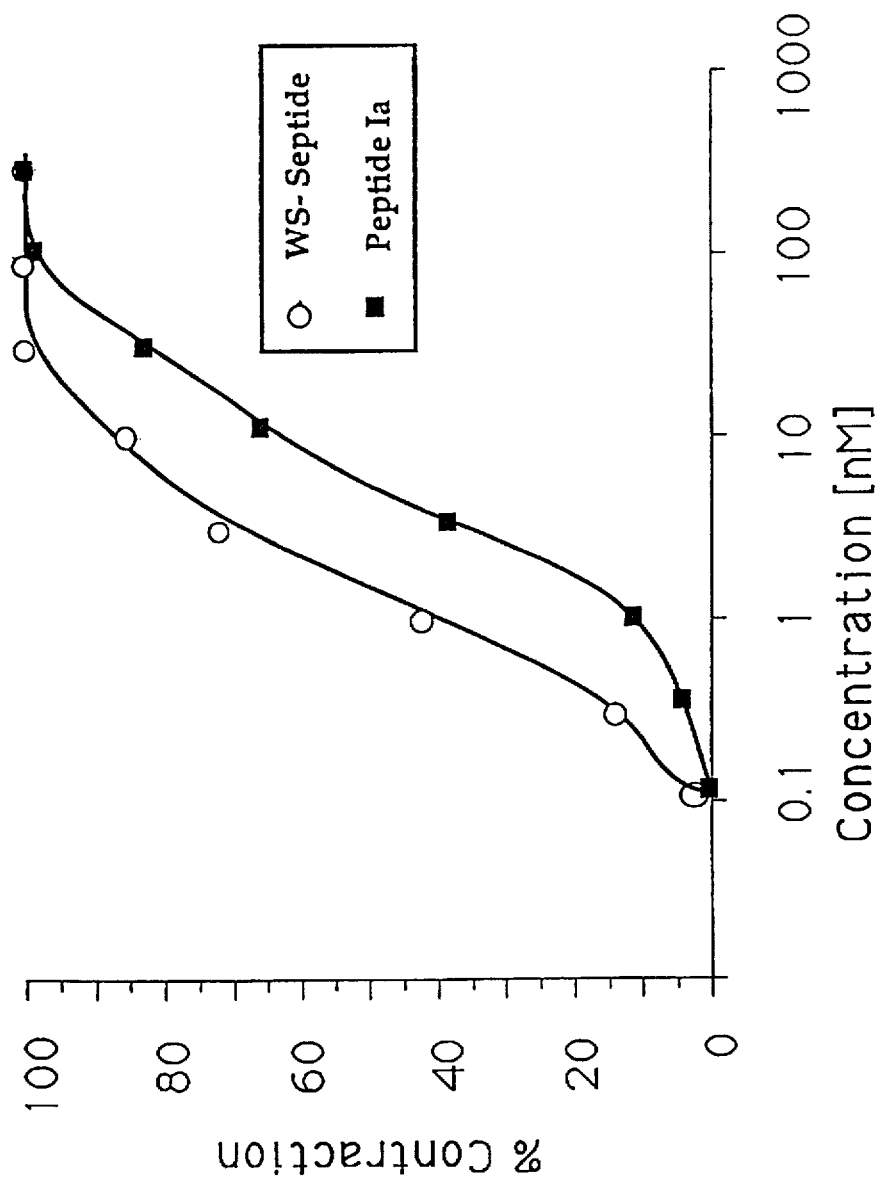
FIG. 3 shows the dose response curves of WS-Septide (according to the prior art) and peptide Ia

FIG. 3 shows the dose response curve of WS septide and peptide Ia.

In order to prove that the high biological activity and selectivity indeed resulted from the cyclization of the peptides, linear analogs IIIa and IIIb were prepared. Analog IIIa contains N-($\beta$-aminoethyl)glycine$^9$ (9th position of Substance P), the $\beta$-amine function being free. Analog IIIb is the nearest linear imitation of peptide Ia, containing the groups $CH_3$—NH-Glur-Arg$^6$ (6th position of Substance P) and Ac-NH—$((CH_2)_3)$-Gly$^9$ (9th position of Substance P). In order to avoid electrical charge influence on the activity, the N-terminus was blocked by acylation and the glutaric end by N-methylation.

The low activity and lack of selectivity of the linear peptides derived from peptide Ia prove the importance of the cyclization in achieving the conformational restriction which is required for increased activity and selectivity.

|  | PEPTIDE STRUCTURE | RECEPTOR SUBTYPES ($EC_{50}$(nM)) | | |
|---|---|---|---|---|
|  |  | NK-1 | NK-2 | NK-3 |
| IIIa | $H_2N$—$(CH_2)_3$<br>\|<br>$CH_3$—CO—Arg—Phe—Phe—N—$CH_2$—CO—Leu—Met—$NH_2$ | 300 | >100,000 | 2000 |
| IIIb | O=C—NH—$CH_3$   Ac—NH—$(CH_2)_3$<br>\|                          \|<br>$(CH_2)_4$—CO—Arg—Phe—Phe—N—$CH_2$—CO—Leu—Met—$NH_2$ | 400 | >100,000 | 2000 |

B. Resistance to Proteases

Figure 2:
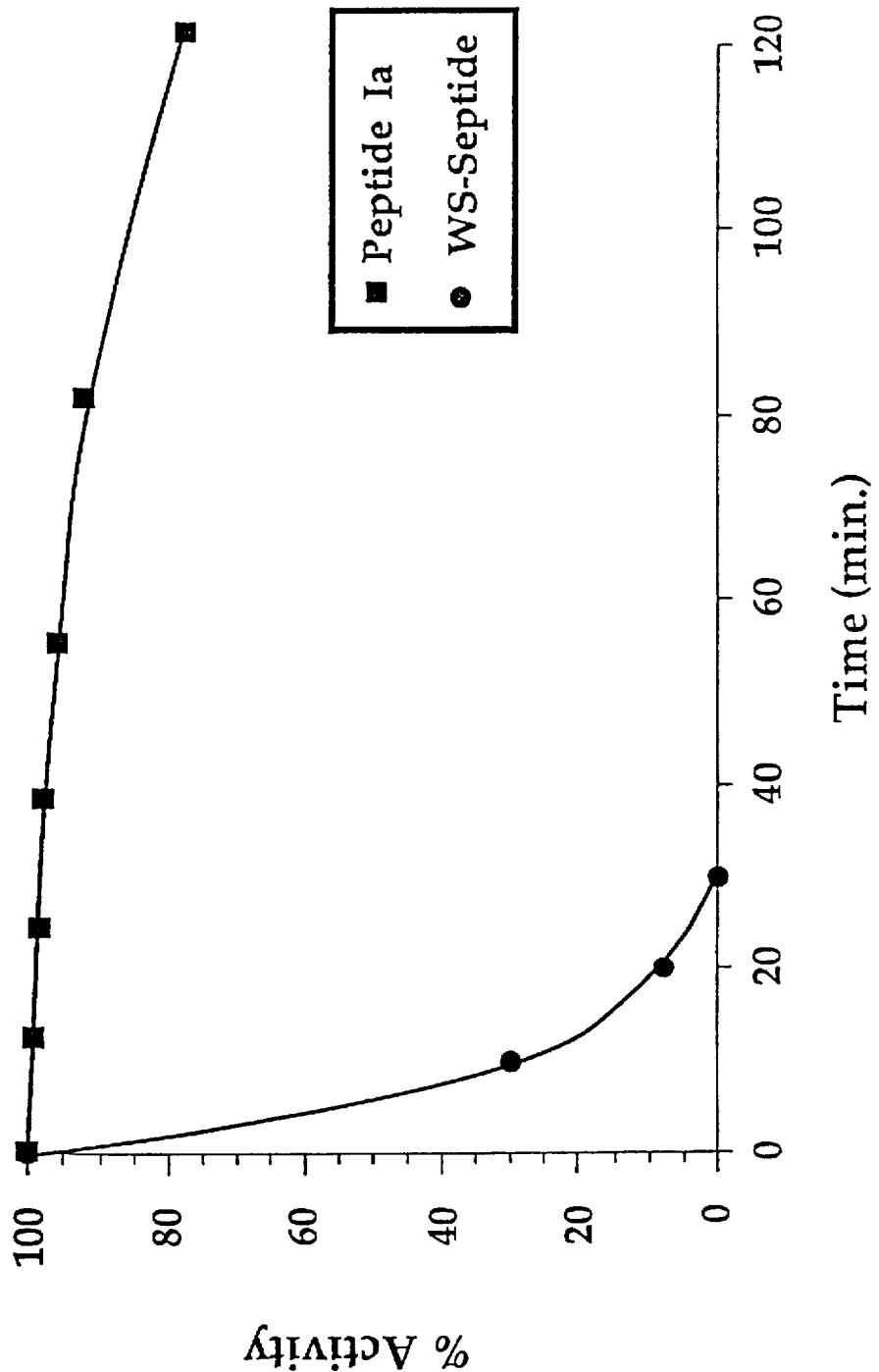
FIG. 2 shows degradation of WS-Septide (according to the prior art) and peptide Ia by parotid slices.

FIG. 2 shows the degradation of WS septide (linear) and peptide Ia in parotid tissue. While the linear WS septide is highly active and selective towards the NK-1 receptor, it is metabolically unstable and activity was lost already after a few minutes (half life=6 min). Peptide Ia retains a 80% activity even after 120 min. of incubation with parotid slices.

The same pattern of behavior can be seen with incubation with liver slices. 50% of the biological activity of the peptide Ia were conserved after 30 min of incubation with the tissue.

We claim:

1. A method for the preparation of cyclic tachykinin peptides of the general formula I:

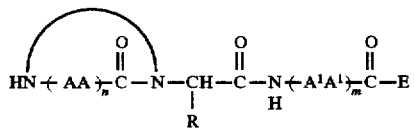
(I)

wherein n designates an integer from 1 to 10 and m designates an integer from 1 to 10, provided that the sum of m and n is no greater than 11;

(AA) and ($A^1A^1$) each designates an amino acid residue of a tachykinin peptide;

R is H, methyl, or an isobutyl group;

E represents a hydroxyl group, a carboxyl protecting group selected from alkoxy, substituted alkoxy or aryloxy or an amino or substituted amino group; and the circled line designates a spacer group of the formula III:

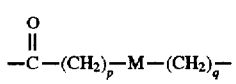
(III)

wherein p and q, each independently designates an integer of from 2 to 10 and wherein one end of the spacer group is attached to the Gly amino acid of the sequence;

said method comprising incorporating an $N^{\alpha}$-ω amino alkylene-amino acid represented by formula Va into a peptide by:

a) preparing a compound of the formula Va:

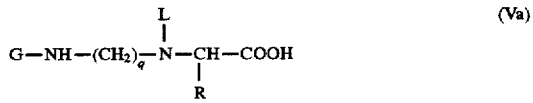
(Va)

wherein R and q are as defined above. G and L each independently represents an alkoxy-, substituted alkoxy- or aryloxy-carbonyl-protecting group by:

(i) reacting an α-halocarboxylic acid of the formula XXII:

(XXII)

wherein R is as defined above and Hal is bromine, chlorine or iodine, with an alkylene diamine of the formula XXIII:

(XXIII)

wherein q is an integer from 2 to 10, to give a compound of the formula XXIV:

(ii)(1) reacting the compound of formula XXIV with a reagent containing the group G selected from the group consisting of halocarbonates, anhydrides or mixed carbonates, to give a compound of the formula XXVI:

or, (2) reacting the compound of formula XXIV with a reagent containing the group G selected from the group consisting of halocarbonates, anhydrides or mixed carbonates, to give a compound of the formula XXVIII:

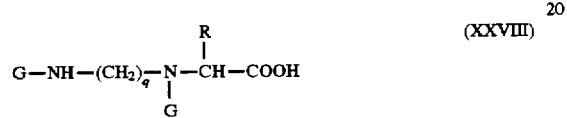

and selectively removing the protecting group G to give a compound of the general formula XXVI; and (iii) reacting the compound of formula XXVI with a reagent containing the group L selected from the group consisting of halocarbonates, anhydrides or mixed carbonates, to give a compound of the formula Va;

b) reacting the compound of formula Va with a compound of the formula:

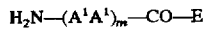

wherein m and ($A^1A^1$) are as defined above, with the proviso that when m is greater than 1 the amino acid residues in the chain may be the same or different, and E represents a hydroxyl group, a carboxyl protecting group selected from alkoxy, substituted alkoxy, aryloxy; an amine or substituted amine group, to give the compound of the formula VIa:

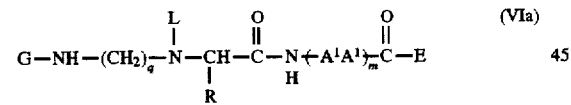

c) selectively removing from the compound of formula VIa, protecting group L, to give a compound of the formula VIIa:

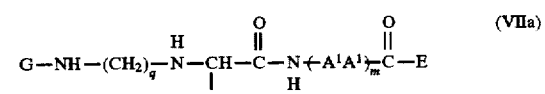

d) reacting the compound of formula VIIa with a compound of the formula VIIIa:

wherein n and (AA) are as defined above with the proviso that when n is greater than 1 the amino acid residues in the chain may be the same or different, and J represents a protecting group selected from the group consisting of alkoxy-, substituted alkoxy- or aryloxy-carbonyl, to give a compound of the formula IXa:

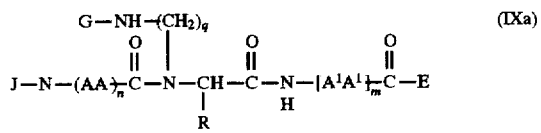

e) selectively removing the protecting group J from the compound of formula IXa, to give a compound of the formula Xa:

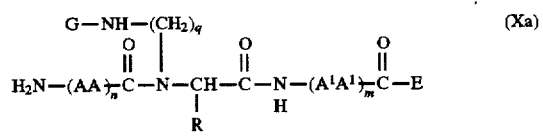

f) reacting the compound of formula Xa with a compound of the formula XIa:

wherein p is an integer from 2 to 10, to give a compound of the formula XIIa:

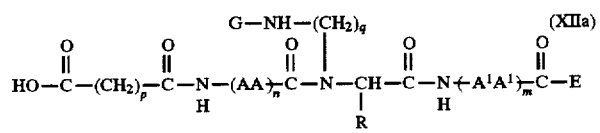

and g) selectively removing the protecting group G from the compound XIIa, to give a compound of the formula XIIIa:

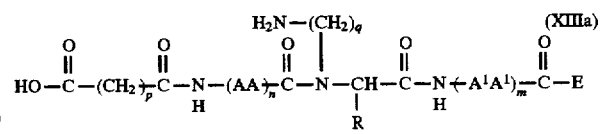

h) cyclizing the peptide by reacting the compound of formula XIIIa with a coupling agent selected from the group consisting of dicyclohexylcarbodiimide (DCC), bis(2-oxo-3-oxazolidinyl)phosphinic chloride (BOP-Cl), benzotriazolyl-N-oxytrisdimethyl aminophosphonium hexafluoro phosphate (BOP), 1-oxo-1-chlorophospholane (Cpt-Cl), hydroxybenzotriazole (HOBT), or mixtures thereof; and i) removing other side-chain protecting groups, to give a compound of the general formula I.

2. A process for the preparation of cyclic tachykinin peptides of general formula II:

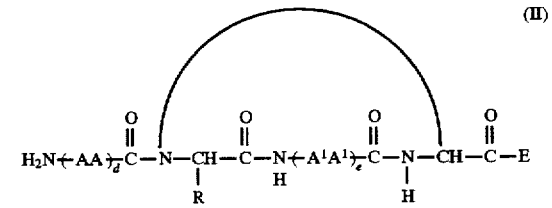

wherein d is 0 or an integer of from 1 to 10, and e is an integer from 1 to 10, provided that the sum of m and n is no greater than 11;

(AA) and ($A^1A^1$) each designates an amino acid residue of a tachykinin peptide;

R is H, methyl or an isobutyl group;

E represents a hydroxyl group, a carboxyl protecting group selected from alkoxy, substituted alkoxy or aryloxy, or an amino or substituted amino group; and the circled line designates a spacer group of formula IV:

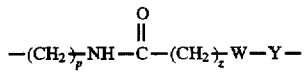  (IV)

wherein p is an integer from 2 to 10;

z is an integer of 0 to 10;

Y designates the side-chain of Asp, Glu, Cys or Met;

W is sulfur or an amino, amide, carboxyl, or disulfide group; and one end of the spacer group is attached to the Gly amino acid of the sequence; said method comprising: incorporating an $N^{\alpha}$-ω amino alkyleneamino acid represented by formula Va into a peptide by the steps of:

a) reacting a compound of the formula XIV:

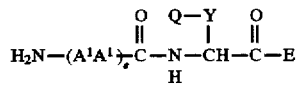  (XIV)

wherein

E, ($A^1A^1$), e and Y are as defined above,

Q represents a protecting group selected from the group consisting of benzyl, acetamidomethyl, tertiary butyl or trityl, alkoxy-, substituted alkoxy- or aryloxy-carbonyl, with a compound of formula Va:

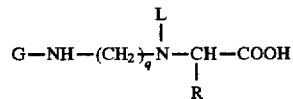  (Va)

wherein R is H, methyl or isobutyl; q is an integer from 2 to 10 and L and G are independently an alkoxy-, substituted alkoxy or aryloxy-carbonyl protecting group, and wherein compound Va is produced by:

(i) reacting an α-halocarboxylic acid of the formula XXII:

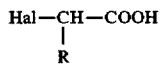  (XXII)

wherein R is as defined above and Hal is bromine, chlorine or iodine, with an alkylene diamine of the formula XXIII:

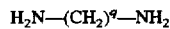  (XXIII)

wherein q is an integer from 2 to 10, to give a compound of the formula XXIV:

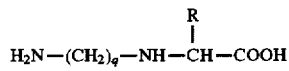  (XXIV)

(ii)(1) reacting the compound of formula XXIV with a reagent containing the group G selected from the group consisting of halocarbonates, anhydrides or mixed carbonates, to give a compound of the formula XXVI:

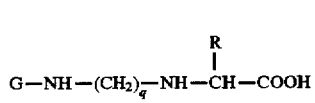  (XXVI)

or (2) reacting the compound formula XXIV with a reagent containing the group G selected from the group consisting of halocarbonates, anhydrides or mixed carbonates, to give a compound of the formula XXVIII:

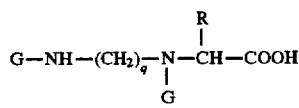  (XXVIII)

and selectively removing the protecting group G from the secondary amino function, to give a compound of the general formula XXVI; and (iii) reacting the compound of formula XXVI with a reagent containing the group L selected from the group consisting of halocarbonates, anhydrides or mixed carbonates, to give a compound of the formula Va:

to give a compound of the formula XV:

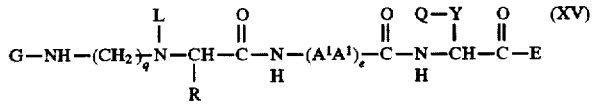  (XV)

b) selectively removing the protecting group L from the compound of formula XV, to give a compound of the formula XVI:

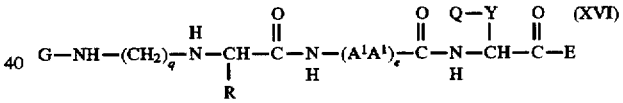  (XVI)

c) reacting the compound of formula XVI with a compound of the formula XVII:

  (XVII)

wherein d and (AA) are as defined above, with the proviso that when d is greater than 1 the amino acid residues in the chain may be the same or different, and P represents a protecting group selected from the group consisting of alkoxy-, substituted alkoxy- or aryloxy-carbonyl, to give a compound of the formula XVIII:

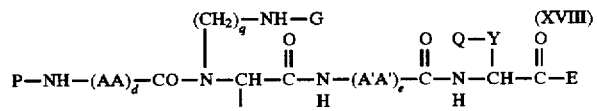  (XVIII)

and d) cyclizing the peptide by the steps of:

(i) where Y is a carboxyl bearing side-chain, selectively removing the protecting groups G and Q from compound XVIII, to give a compound of the formula XIX:

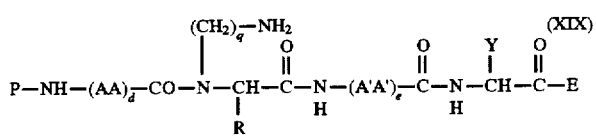

cyclizing compound XIX with a coupling agent selected from the group consisting of dicyclohexylcarbodiimide (DCC), bis(2-oxo-3-oxazolidinyl)phosphinic chloride (BOP-Cl), benzotriazolyl-N-oxytrisdimethylamino phosphonium hexafluoro phosphate (BOP), 1-oxo-1-chlorophospholane (Cpt-Cl), hydroxybenzotriazole (HOBT), or mixtures thereof and removing protecting group P and other side-chain protecting groups to give a compound of the general formula II; or (ii) where Y is a side-chain bearing an SH-functional group, selectively removing protecting group G, reacting the resulting compound with a compound of the formula XX:

wherein z is an integer of from 1 to 10 and W is a functional group capable of reacting with said nucleophilic group, to give a compound of the formula XXI:

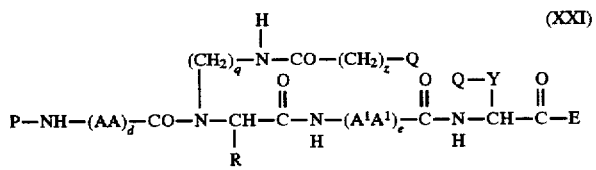

selectively removing the protecting group Q, whereupon cyclization occurs, and removing the protecting group P and other side-chain protecting groups from compound XXI to give a compound of the general formula II.

3. The method of claim 1 wherein the carboxyl protecting group E is covalently attached to an insoluble polymeric support.

4. The method of claim 1 wherein G and L are each selected from the group consisting of benzyloxycarbonyl, t-butyloxycarbonyl and fluorenylmethoxycarbonyl.

5. The method of one of claims 3, or 4, wherein G is t-butyloxycarbonyl and L is fluorenylmethoxycarbonyl.

6. The method of claim 1 wherein J represents a protecting group selected from the group consisting of t-butyloxycarbonyl, fluorenylmethoxycarbonyl and benzyloxycarbonyl.

7. The method of claim 1, wherein the sum of m and n is 6.

8. The method of claim 1 wherein q is 3 and p is 3 or 4.

9. The method of claim 1 wherein formula I includes a terminal carboxyl sequence of -Phe-X-Gly-Leu-Met-NH$_2$ where X is Phe or Val.

10. The method of claim 1 wherein cyclic peptides of the following formulae are prepared:

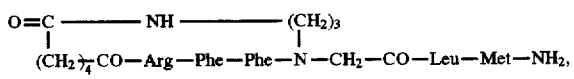

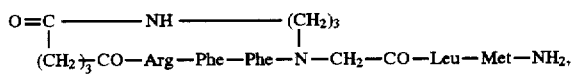

or

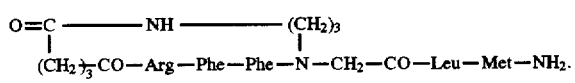

11. The method of claim 2, wherein G is t-butyloxycarbonyl and L is fluorenylmethoxycarbonyl.

12. The method of claim 2, wherein P is replaced by acetyl.

13. The method of claim 2, wherein E is covalently bound to an insoluble polymeric support.

14. The method of claim 2, wherein in step (d)(ii) W is selected from the group consisting of halogen atoms, O-p-toluenesulphonyl, O-methanesulphonyl and O-trifluoromethanesulphonyl.

15. The method of claim 2 wherein R is H.

16. The method of claim 2 wherein R is methyl.

17. The method of claim 2 wherein R is isobutyl.

18. The method of claim 2 wherein the following cyclic peptide is prepared:

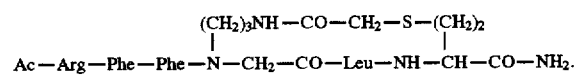

19. The method of claim 2, wherein the sum of m and n is 6.

20. The method of claim 2, wherein M is sulfur and p is 3.

21. The method of claim 2 wherein formula II includes a terminal carboxyl sequence of -Phe-X-Gly-Leu-Met-NH$_2$ where X is Phe or Val.

* * * * *

UNITED STATES PATENT AND TRADEMARK OFFICE
CERTIFICATE OF CORRECTION

PATENT NO. : 5,723,575
DATED : March 3, 1998
INVENTOR(S) : C. Gilon et al.

It is certified that error appears in the above-indentified patent and that said Letters Patent is hereby corrected as shown below:

Column 29, lines 61-64: formula III should appear as follows:

Column 31, lines 51-54: formula VIIa should appear as follows:

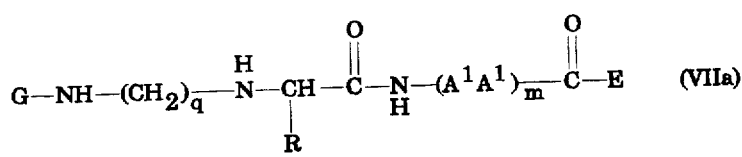

UNITED STATES PATENT AND TRADEMARK OFFICE
CERTIFICATE OF CORRECTION

PATENT NO. : 5,723,575

DATED : March 3, 1998

INVENTOR(S) : C. Gilon et al.

It is certified that error appears in the above-indentified patent and that said Letters Patent is hereby corrected as shown below:

Column 33, line 55, formula XXIII should read as follows:

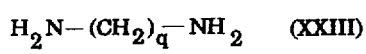

$$H_2N-(CH_2)_q-NH_2 \quad (XXIII)$$

Column 35, lines 26-31, formula XXI should read as follows:

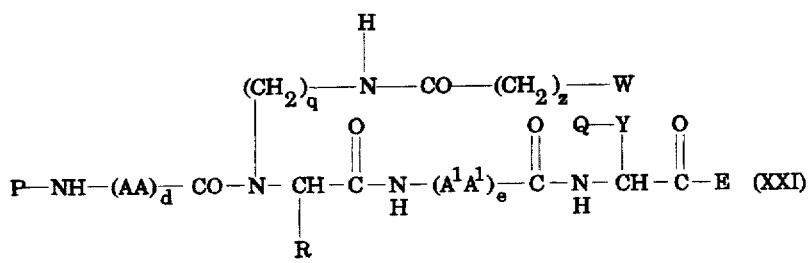

UNITED STATES PATENT AND TRADEMARK OFFICE
CERTIFICATE OF CORRECTION

PATENT NO. : 5,723,575

DATED : March 3, 1998

INVENTOR(S) : C. Gilon et al.

It is certified that error appears in the above-indentified patent and that said Letters Patent is hereby corrected as shown below:

Column 36, lines 15-18 should read as follows:

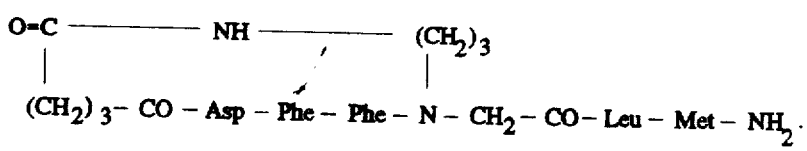

Signed and Sealed this

Twenty-fifth Day of August, 1998

Attest:

Attesting Officer

BRUCE LEHMAN

Commissioner of Patents and Trademarks